(12) United States Patent
Hestad et al.

(10) Patent No.: US 8,337,530 B2
(45) Date of Patent: Dec. 25, 2012

(54) POLYAXIAL PEDICLE SCREW WITH INCREASED ANGULATION

(75) Inventors: Hugh D. Hestad, Edina, MN (US); Jack A. Dant, St. Paul, MN (US); Eric J. Lundequam, Plymouth, MN (US); Eric P. Jerke, Bloomington, MN (US); Deborah L. Hoch, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 55 days.

(21) Appl. No.: 13/044,174

(22) Filed: Mar. 9, 2011

(65) Prior Publication Data

US 2012/0232598 A1 Sep. 13, 2012

(51) Int. Cl.
*A61B 17/88* (2006.01)
*A61B 17/70* (2006.01)

(52) U.S. Cl. ........................................ 606/279; 606/264
(58) Field of Classification Search .......... 606/246–279, 606/305, 86 A
See application file for complete search history.

(56) References Cited

U.S. PATENT DOCUMENTS

| | | | |
|---|---|---|---|
| 6,074,391 A | 6/2000 | Metz-Stavenhagen | |
| 6,520,963 B1 | 2/2003 | McKinley | |
| 6,736,820 B2 | 5/2004 | Biedermann | |
| 6,974,460 B2 | 12/2005 | Carbone et al. | |
| 6,981,973 B2 | 1/2006 | McKinley | |
| 7,081,116 B1 | 7/2006 | Carly | |
| 7,081,117 B2 * | 7/2006 | Bono et al. | 606/300 |
| 7,264,621 B2 | 9/2007 | Coates et al. | |
| 7,377,923 B2 | 5/2008 | Purcell et al. | |
| 7,503,924 B2 * | 3/2009 | Lee et al. | 606/272 |
| 7,588,575 B2 * | 9/2009 | Colleran et al. | 606/86 A |
| 7,618,442 B2 * | 11/2009 | Spitler et al. | 606/266 |
| 7,635,380 B2 * | 12/2009 | Zucherman et al. | 606/267 |
| 7,875,065 B2 * | 1/2011 | Jackson | 606/305 |
| 8,016,862 B2 * | 9/2011 | Felix et al. | 606/270 |
| 8,062,340 B2 * | 11/2011 | Berrevoets et al. | 606/270 |
| 8,162,989 B2 * | 4/2012 | Khalili | 606/266 |
| 8,167,910 B2 * | 5/2012 | Nilsson | 606/264 |
| 8,221,472 B2 * | 7/2012 | Peterson et al. | 606/270 |
| 2003/0153921 A1 * | 8/2003 | Stewart et al. | 606/72 |
| 2003/0171755 A1 | 9/2003 | Moseley et al. | |
| 2005/0033296 A1 * | 2/2005 | Bono et al. | 606/61 |
| 2005/0080420 A1 | 4/2005 | Farris | |
| 2005/0154391 A1 | 7/2005 | Doherty et al. | |
| 2005/0159750 A1 | 7/2005 | Doherty | |
| 2005/0177154 A1 * | 8/2005 | Moumene et al. | 606/61 |
| 2005/0228382 A1 * | 10/2005 | Richelsoph et al. | 606/61 |

(Continued)

*Primary Examiner* — Alvin Stewart
*Assistant Examiner* — Stuart S Bray
(74) *Attorney, Agent, or Firm* — Seager Tufte & Wickhem LLC

(57) ABSTRACT

A polyaxial bone anchor including a housing and a bone screw. A bottom surface of the housing includes an aperture that defines an angulation limit of the bone screw for each azimuthal angle around a longitudinal axis of the housing. The aperture is V-shaped, with the V-shape having converging side walls that define a low-angulation direction near their intersection and a high-angulation direction opposite the low-angulation direction. In some cases, the angulation limit of the bone screw is generally constant over a range of azimuthal angles centered around the high-angulation direction. The housing may be modular, including tabs on one component that are plastically deformed to engage a lip on another component. During assembly, a mandrel advances longitudinally along a bore in the housing, and forces the tabs radially outward toward the lip to a radially outward plastically deformed state.

10 Claims, 25 Drawing Sheets

U.S. PATENT DOCUMENTS

| | | |
|---|---|---|
| 2006/0036242 A1* | 2/2006 | Nilsson et al. .................. 606/61 |
| 2006/0036244 A1* | 2/2006 | Spitler et al. .................... 606/61 |
| 2006/0111715 A1* | 5/2006 | Jackson ........................... 606/61 |
| 2006/0235389 A1 | 10/2006 | Albert et al. |
| 2006/0235393 A1* | 10/2006 | Bono et al. ...................... 606/61 |
| 2007/0118123 A1 | 5/2007 | Strausbaugh et al. |
| 2008/0021473 A1 | 1/2008 | Butler et al. |
| 2008/0161859 A1* | 7/2008 | Nilsson .......................... 606/266 |
| 2008/0243185 A1* | 10/2008 | Felix et al. .................... 606/246 |
| 2009/0093844 A1* | 4/2009 | Jackson ......................... 606/254 |
| 2009/0105756 A1* | 4/2009 | Richelsoph .................... 606/246 |
| 2009/0163961 A1 | 6/2009 | Kirschman |
| 2009/0163962 A1* | 6/2009 | Dauster et al. ................ 606/305 |
| 2009/0318972 A1* | 12/2009 | Jackson ......................... 606/264 |
| 2010/0063545 A1* | 3/2010 | Richelsoph .................... 606/264 |
| 2010/0145394 A1 | 6/2010 | Harvey et al. |
| 2010/0160977 A1 | 6/2010 | Gephart et al. |
| 2010/0204735 A1 | 8/2010 | Gephart et al. |
| 2010/0204737 A1* | 8/2010 | Bae et al. ....................... 606/279 |
| 2010/0331883 A1* | 12/2010 | Schmitz et al. ............... 606/249 |
| 2011/0098747 A1* | 4/2011 | Donner et al. ................. 606/264 |
| 2011/0190822 A1* | 8/2011 | Spitler et al. .................. 606/264 |
| 2011/0196429 A1* | 8/2011 | Hua ................................ 606/279 |
| 2011/0213419 A1* | 9/2011 | Richelsoph .................... 606/264 |
| 2011/0245872 A1* | 10/2011 | Nilsson ......................... 606/250 |
| 2012/0029569 A1* | 2/2012 | Iott et al. ....................... 606/264 |
| 2012/0071930 A1* | 3/2012 | Chervitz et al. ............... 606/279 |

* cited by examiner ature and a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second a second

POLYAXIAL PEDICLE SCREW WITH INCREASED ANGULATION

TECHNICAL FIELD

The disclosure is directed to vertebral anchors for use with orthopedic fixation systems. More particularly, the disclosure is directed to polyaxial bone anchors including structures for controlling the angulation limit of a bone screw as a function of direction.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or restore motion of the spinal column.

One possible method of treating these conditions is to immobilize a portion of the spine to allow treatment. Traditionally, immobilization has been accomplished by rigid stabilization. For example, in a conventional spinal fusion procedure, a surgeon restores the alignment of the spine or the disc space between vertebrae by installing a rigid fixation rod between pedicle screws secured to adjacent vertebrae. Bone graft is placed between the vertebrae, and the fixation rod cooperates with the screws to immobilize the two vertebrae relative to each other so that the bone graft may fuse with the vertebrae.

Dynamic stabilization has also been used in spinal treatment procedures. Dynamic stabilization does not result in complete immobilization, but instead permits a degree of mobility of the spine while also providing sufficient support and stabilization to effect treatment. One example of a dynamic stabilization system is the Dynesys® system available from Zimmer Spine, Inc. of Minneapolis, Minn. Such dynamic stabilization systems typically include a flexible construct extending between pedicle screws installed in adjacent vertebrae of the spine.

In some cases, it may be desirable to use an anchor that provides a relatively large angulation (i.e., the angle at which the bone screw is tilted with respect to a longitudinal axis of the anchor housing) over a continuous range of azimuthal angles around the longitudinal axis of the anchor housing.

SUMMARY

The disclosure is directed to several alternative designs, materials and methods of assembling polyaxial bone anchor structures and assemblies.

Accordingly, one illustrative embodiment is a polyaxial bone anchor. The polyaxial bone anchor includes a housing and a bone screw. The housing has an upper end, a lower end and a bore extending through the housing from the upper end to the lower end. The bore opens out at the lower end at a lower opening. The housing includes a channel configured for receiving an elongate stabilization member therethrough. The elongate stabilization member extends from a first side surface of the housing to a second side surface of the housing opposite the first side surface transverse to the bore. The bone screw includes a head and a shank extending from the head. The head of the bone screw is positionable in the housing. The shank extends from the lower end of the housing. The lower opening of the bore defines an angulation limit of the bone screw for each azimuthal angle around a longitudinal axis of the bore. The lower opening of the bore is generally V-shaped. The V-shape has angled side walls. The angled side walls define a low-angulation direction proximate their intersection and define a high-angulation direction opposite the low-angulation direction.

Another illustrative embodiment is a polyaxial bone anchor. The polyaxial bone anchor includes a housing and a bone screw. The housing has an upper end, a lower end and a bore extending through the housing from the upper end to the lower end. The bore opens out at the lower end at a lower opening. The housing includes a channel configured for receiving an elongate stabilization member therethrough. The elongate stabilization member extends from a first side surface of the housing to a second side surface of the housing opposite the first side surface transverse to the bore. The bone screw includes a head and a shank extending from the head. The head of the bone screw is positionable in the housing. The shank extends from the lower end of the housing. The lower opening of the bore defines an angulation limit of the bone screw for each azimuthal angle around a longitudinal axis of the bore. The angulation limit has a maximum value in a high-angulation direction. The angulation limit is generally constant over an azimuthal range centered about the high-angulation direction. For a low-angulation direction opposite the high-angulation direction, the angulation limit is less than the maximum value.

Another illustrative embodiment is a method of assembling a polyaxial bone anchor. The method includes providing an upper housing having a bore extending vertically therethrough, the upper housing including a plurality of plastically deformable tabs circumferentially around a lower end of the upper housing, each tab having a portion that extends radially outward beyond a radial extent of the bore and a portion that extends radially inside the bore; providing a lower housing having a lip proximate an upper end of the lower housing; placing the lower housing beneath the upper housing so that the lip is radially adjacent the tabs; inserting a mandrel downward through the bore in the upper housing; forcing the tabs radially outward with the mandrel, each tab on the upper housing plastically deforming radially outward and engaging the lip on the lower housing; and withdrawing the mandrel from the upper housing.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
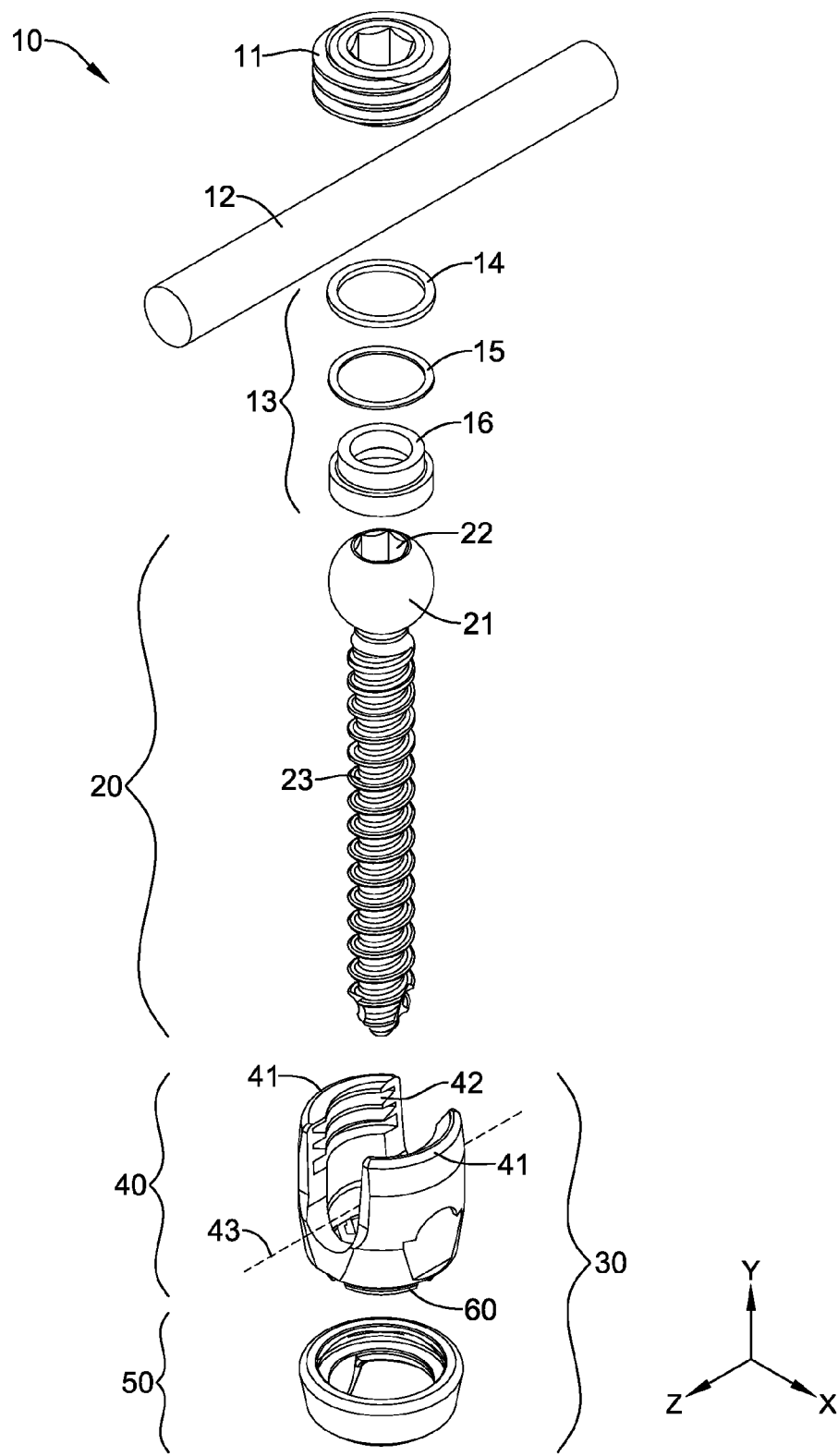
FIG. 1 is an exploded view of components of an exemplary polyaxial bone anchor.
Figure 2:
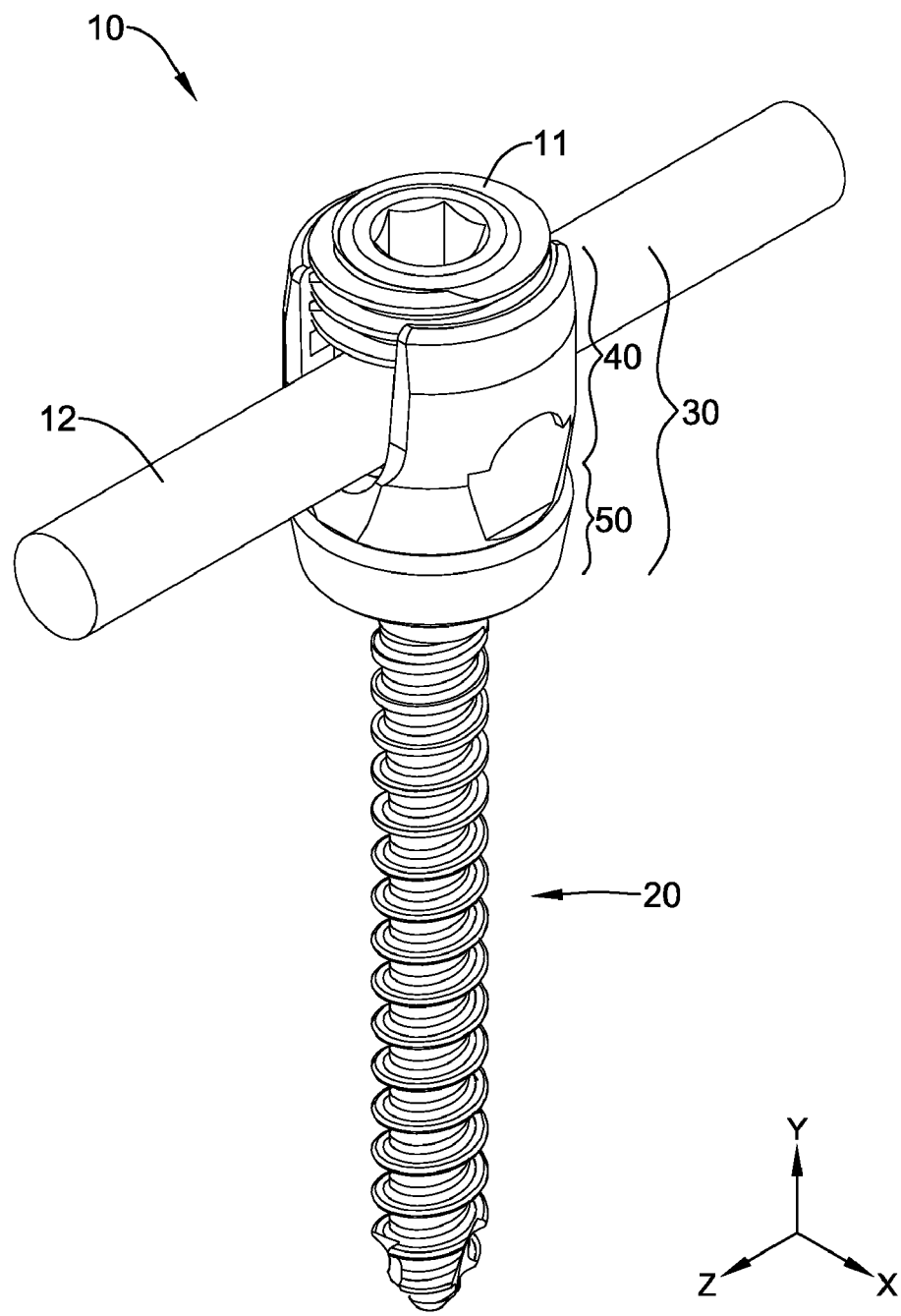
FIG. 2 is a perspective view of the polyaxial bone anchor of FIG. 1, viewed from above.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is an exploded view illustrating components of an exemplary polyaxial bone anchor 10. In use, the bone anchor 10, which may be screwed into a vertebra, may serve to couple a rod 12 or other elongate member extending along a portion of a spinal column. The rod or elongate member 12 may fit into a U-shaped channel 43 formed by opposing arms 41 from the top of the housing 30. The bone anchor 10 may include particular degrees of adjustability that ensure that the screws and elongate member 12 may be locked down at the particular locations and orientations desired by the practitioner.

It should be noted that in practice, even though the screw 20 may be first screwed into the vertebra, then the housing 30 may be adjusted to accommodate the rod 12 in the U-shaped channel 43, in this document we examine the elements from the point of view of the housing 30, so that the screw 20 may be referred to as being adjustable with respect to the housing 30.

In particular, the bone anchor 10 may allow for angular deviation of the bone screw 20 away from the axial orientation shown in FIG. 1. Such an angular deviation may be referred to as "angulation", and desired angulations may exceed 35 degrees, 40 degrees, 45 degrees, or more, in some instances.

In addition, the bone anchor 10 may allow for angulation in a variety of directions, not just in one direction. These directions are measured with respect to a longitudinal axis of the bone anchor 10, which in FIG. 1 extends from the top to the bottom of the drawing. The longitudinal axis may be coaxial with the threaded bore of the housing 30. These directions may be referred to as an "azimuthal angle", and may extend from 0 degrees to 360 degrees around the longitudinal axis of the bone anchor 10.

The allowed angulation of the bone anchor 10 may vary as a function of azimuthal angle, so that angulation may be more restricted in one direction over another. In other words, the bone anchor 10 may be configured such that the maximum angulation of the bone screw 20 relative to the longitudinal axis of the housing 30 may be greater at a first azimuthal angle than at a second azimuthal angle. In general, it may be difficult to allow relatively large angulation in all azimuthal directions, because the housing 30 of the bone anchor 10 may lose its ability to clamp onto the head 21 of the bone screw 20.

In the bone anchor 10 described herein, there is particular attention paid to the amount of angulation that is allowed (referred to herein as an "angulation limit") as a function of azimuthal angle. These aspects of angulation limit versus azimuthal angle are discussed in detail, following a brief discussion of the various elements shown in the exploded view of FIG. 1, and also shown in the assembled views of FIGS. 2-7.

The bone anchor 10 may be delivered to the practitioner in a semi-assembled state. The housing 30 may have a bore that extends longitudinally through the housing 30, generally coaxial with the longitudinal axis of the bone anchor 10.

In the exemplary design of FIG. 1, the housing 30 may be modular, thus formed of multiple components coupled together. For example, the housing 30 may include two components that are longitudinally adjacent to each other, namely an upper housing 40 and a lower housing 50. In some cases, the lower housing 50 may be rotatable relative to the upper housing 40, such that the high angular direction 54 (see FIG.

3) may be positioned at any desired angular orientation relative to the axis of the U-shaped channel 43 of the upper housing 40. In other cases, the housing 30 may alternatively be of a unitary construction, formed of a singular element.

Prior to assembly, the screw 20 may be dropped downward into the top of the housing 30. Alternatively, the screw 20 may be bottom-loaded into the upper housing 40, and then the lower housing 50 may be coupled onto the upper housing 40, so that the screw 20 is held in place between the coupled upper housing 40 and lower housing 50.

The screw 20 may have a threaded shank 23 that extends out the bottom opening of the housing 30, and may have a head 21 that is sized such that the head 21 cannot pass through the opening at the bottom of the housing 30. The head 21 of the screw 20 may be generally spherical in shape, so that it may pivot with respect to the housing 30.

The head 21 of the screw 20 may be held in place by a retainer assembly 13, which may prevent the screw 20 from being pulled upward out of the housing 30. The retainer assembly 13 may allow pivoting of the screw head 21 with respect to the housing 30. The retainer assembly 13 is typically in the form of one or more rings having a central aperture, which may allow the practitioner to insert a screwdriver through the aperture of the rings to engage a driver interface such as a keyed portion 22 on the head 21 of the screw 20. The exemplary retainer assembly 13 in FIG. 1 may include a seat 16 that may contact the head 21 of the screw 20, a biasing member or wave washer 15, and a retainer ring 14 farthest away from the screw head 21. The seat 16 may include a concave annular region that has a radius of curvature matched to that of the screw head 21, so that when the screw 20 is pivoted, it may remain held in place by the seat 16.

To lock the elements in place, the practitioner may screw the fastener or set screw 11 into threads 42 at the upper portion of the housing 30, which may force the rod or elongate member 12 against the upper surface of seat 16, and in turn may force the seat 16 against the head 21 of the screw 20. Prior to final tightening of the set screw 11, the biasing member 15 may cause the seat 16 to frictionally engage the head 21 of the screw 20 to resist movement of the housing 30 with respect to the screw 20. After tightening of the set screw 11, the frictional force between the seat 16 of the retainer assembly 13 and the head 21 of the screw 20 is sufficient to lock the screw 20 in place with respect to the housing 30. In the exemplary design of FIGS. 1-7, the U-shaped channel 43 is deep enough so that the set screw 11 does not force the rod 12 against the bottom of the U-shaped channel 43. Alternatively, the retainer assembly 13 may be omitted, and the set screw 11 may force the rod 12 directly against the head 21 of the screw 20 to secure the screw 20 in place.

It is instructive to further describe two additional aspects of the housing 30, one being the way the angulation limit is controlled as a function of azimuthal angle, and the other being the way the upper 40 and lower 50 housings are assembled. The angulation is discussed first.

The housing 30 may have a bottom surface 51 with a shaped opening 56. The perimeter of the opening 56 may directly affect how much angulation may be achieved in a given direction, because the shank 23 of the screw 20 beneath the head 21 may engage the perimeter at the angulation limit, preventing further angulation. By tailoring the perimeter of the opening 56, one may control the angulation limit as a function of azimuthal angle. Note that one still needs a particular amount of surface area on the bottom surface to engage the head 21 of the screw 20; one cannot simply make the opening 56 arbitrarily large in all directions, because the head 21 of the screw 20 would fall through the opening 56.

Figure 3:
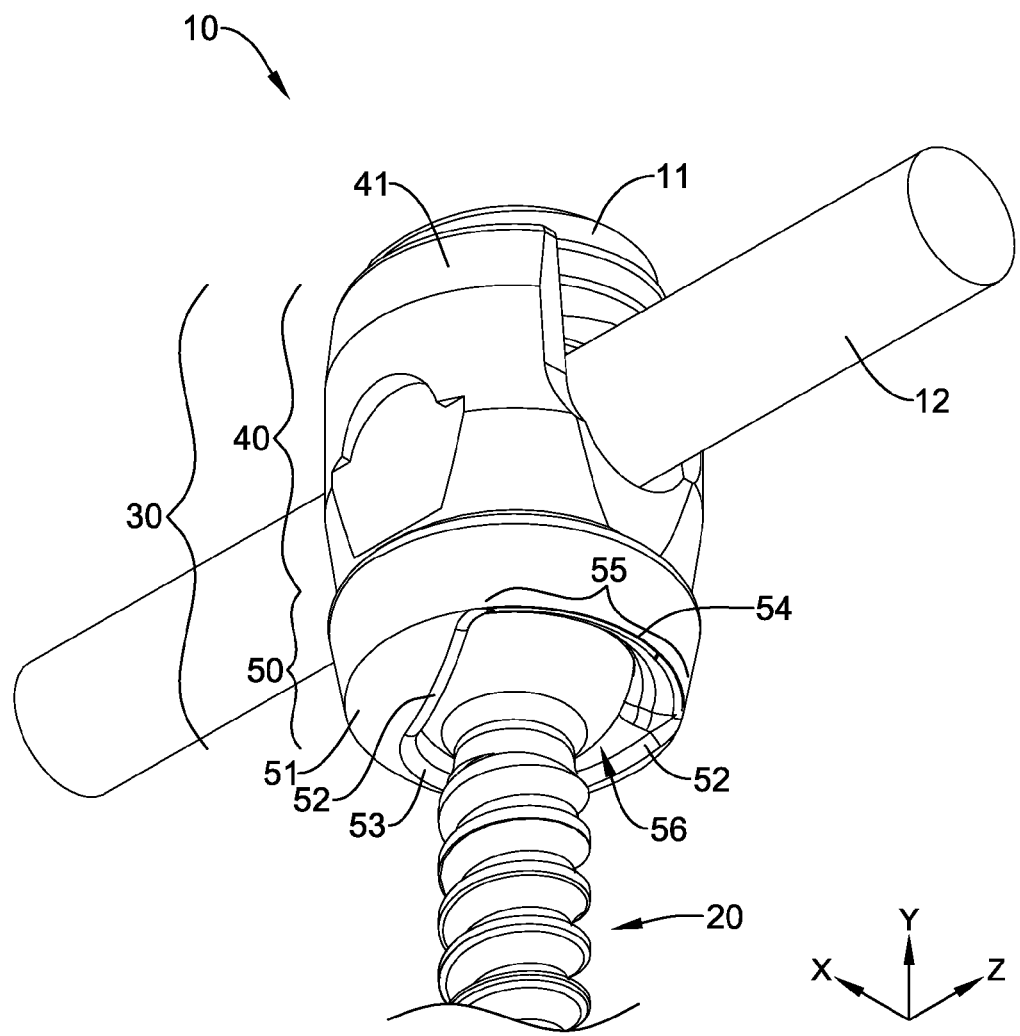
FIG. 3 is a perspective view of the polyaxial bone anchor of FIGS. 1-2, viewed from below.
Figure 4:
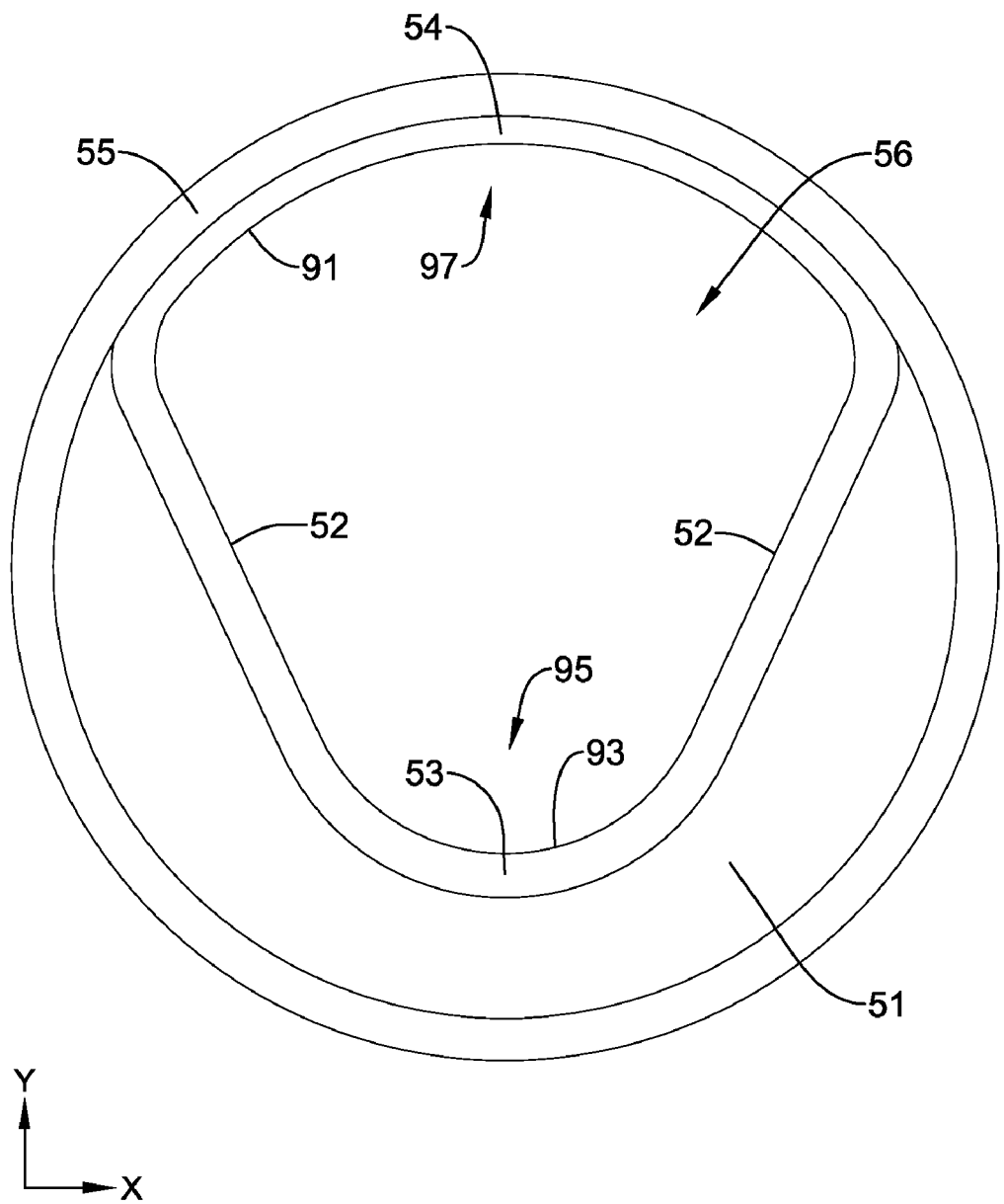
FIG. 4 is a bottom view of the polyaxial bone anchor of FIGS. 1-3.
Figure 5:
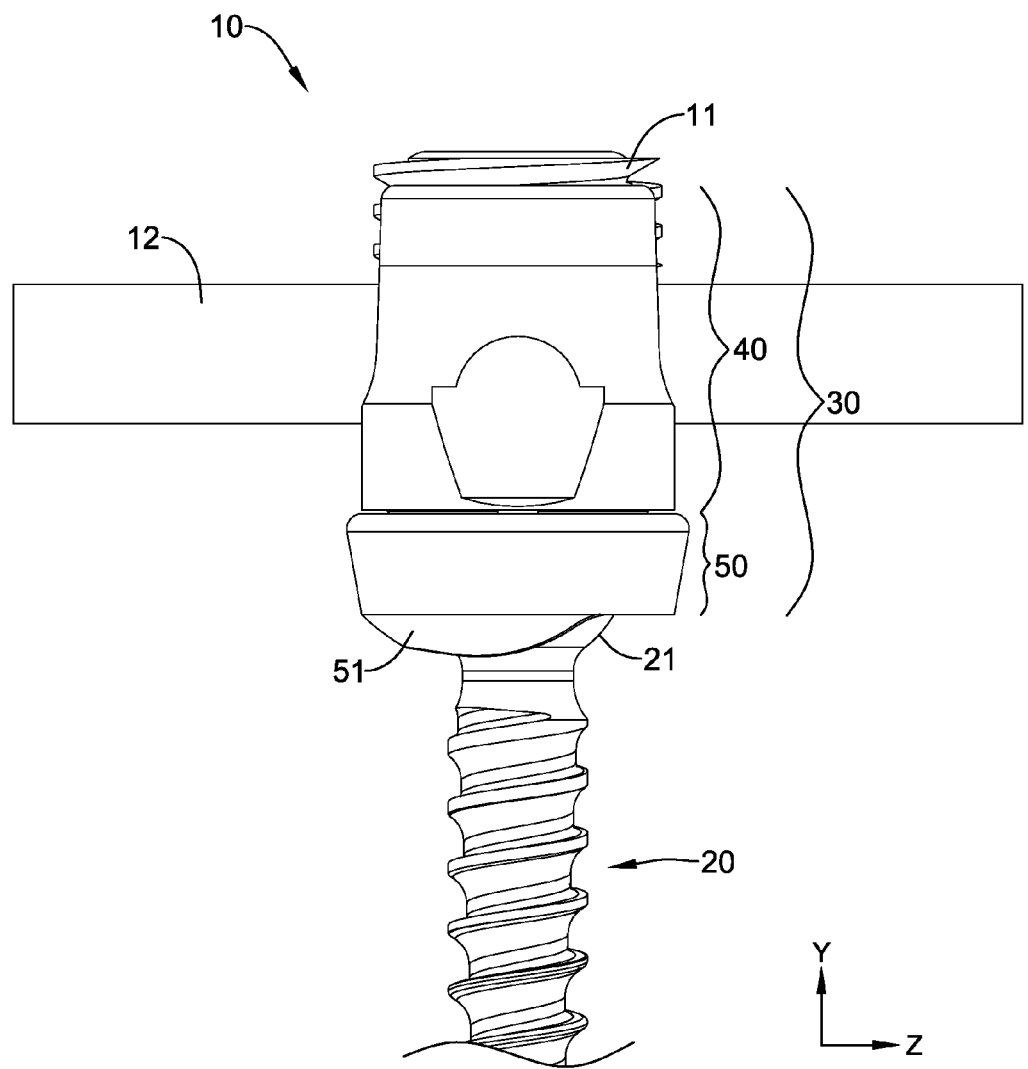
FIG. 5 is a plan view of the polyaxial bone anchor of FIGS. 1-4, viewed from a side.
Figure 6:
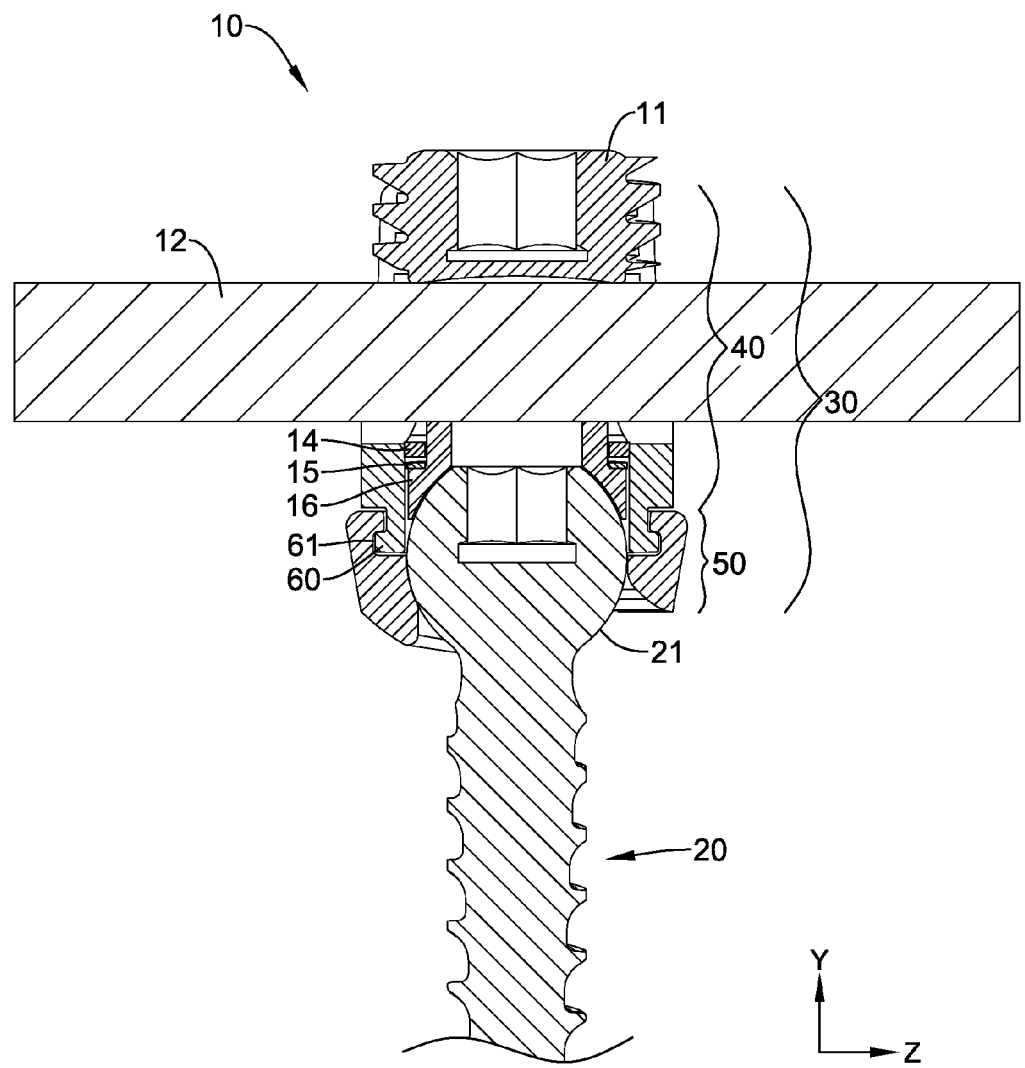
FIG. 6 is a cross-sectional view of the polyaxial bone anchor of FIGS. 1-5.
Figure 7:
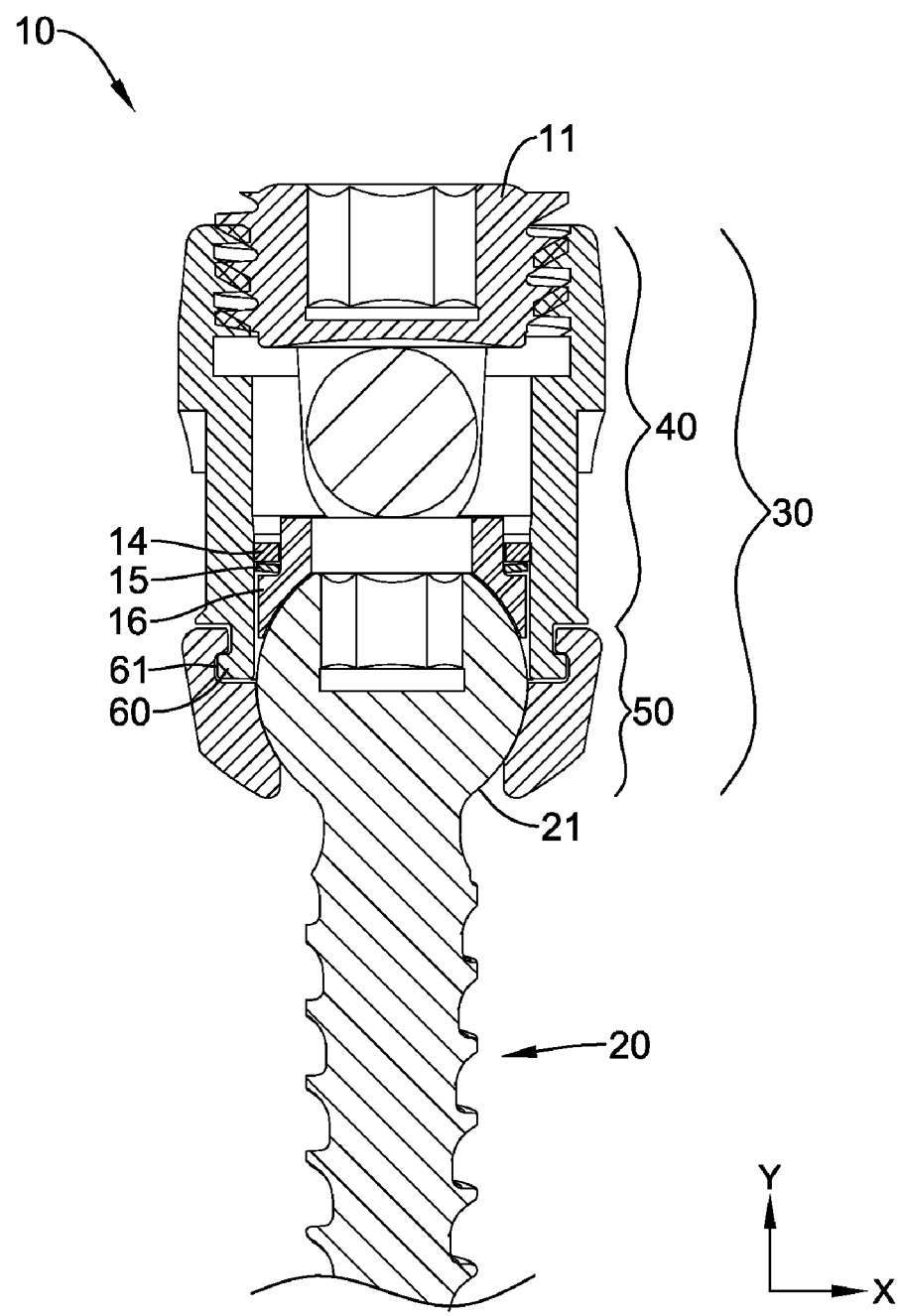
FIG. 7 a cross-sectional view of the polyaxial bone anchor of FIGS. 1-6, transverse to the cross-sectional view of FIG. 6.

In the exemplary bone anchor 10 of FIGS. 1-7, shown most clearly in FIGS. 3 and 4, the opening 56 in the bottom surface 51 may be generally V-shaped, with angled or converging side walls 52. At the "closed" end of the V-shape (i.e., the end in which the side walls 52 are closer together), the angled side walls 52 define a low-angulation direction 53. Opposite the low-angulation direction 53, at the "open" end of the V-shape (i.e., the end in which the side walls 52 are further apart), the angled side walls 52 define a high-angulation direction 54. In FIG. 3, the low-angulation direction is toward the bottom-left corner of the figure, while the high-angulation direction is toward the top-right corner of the figure. In FIG. 4, the high-angulation direction 54 is at the top of the figure, while the low-angulation direction 53 is at the bottom of the figure. The high-angulation direction 54 (at the 12 o'clock position, or 0 degrees) may be opposite (i.e. 180 degrees from) the low-angulation direction 53 (at the 6 o'clock position, or 180 degrees).

The shape of the opening 56 at the bottom surface 51 of the lower housing 50 may alternatively be described as follows. The opening 56 may be defined by converging planar side walls 52, a first arcuate end wall 91 extending between the side walls 52 at a first end 97 proximate the high-angulation direction 54, a second arcuate end wall 93 extending between the side walls 52 at a second end 93 proximate the low-angulation direction 53. The arc length of the first arcuate end wall 91 may be greater than the arc length of the second arcuate end wall 93. Furthermore, the first arcuate end wall 91 may have a radius of curvature greater than a radius of curvature of the second arcuate end wall 93.

In FIG. 3, the screw 20 is pointing directly downward, so that as drawn, it has an angulation of zero. In other words, the longitudinal axis of the screw 20 is coaxial with the longitudinal axis of the housing 30.

In the low-angulation direction 53, the screw 20 may pivot a particular amount from the longitudinal axis of the housing 30, such as less than 5 degrees, about 5 degrees, between 5 and 10 degrees, about 10 degrees, between 10 and 15 degrees, about 15 degrees, between 15 and 20 degrees, about 20 degrees, between 20 and 25 degrees, about 25 degrees, between 25 and 30 degrees, less than 30 degrees, less than 25 degrees, less than 20 degrees, less than 15 degrees, less than 10 degrees, or less than 5 degrees, in some instances. In some instances, each of these numerical values or ranges may represent the angulation limit in the low-angulation direction 53.

In the high-angulation direction 54, the screw 20 may also pivot a particular amount from the longitudinal axis of the housing 30, such as about 30 degrees, more than 30 degrees, about 35 degrees, more than 35 degrees, about 40 degrees, more than 40 degrees, about 45 degrees, more than 45 degrees, about 50 degrees, or more than 50 degrees, in some instances. In some instances, each of these numerical values or ranges may represent the angulation limit in the high-angulation direction 54.

At azimuthal angles between the low-angulation direction 53 and the high-angulation direction 54, the angulation limit may be largely determined by the shape of the angled side walls 52. The side walls 52 may be relatively straight or planar, may bow inward, may bow outward, or may have a more complicated shape. In some cases, the angulation limit achieves a minimum value at an azimuthal angular position between the high-angulation direction and the low-angulation direction. In other cases, the angulation limit achieves a minimum value at the low-angulation direction.

In the exemplary design shown most clearly in FIGS. 3 and 4, there is a range of azimuthal angles R, centered around the high-angulation direction 54, over which the angulation limit is essentially constant and essentially equal to that at the high-angulation direction 54. Such a range of azimuthal angles R over which the angulation limit is constant may be caused by a ridge 55 or arcuate portion along the perimeter of the aperture on the bottom surface 51 of the housing 30.

Proximate the high-angulation direction 54, the range of azimuthal angles R over which the angulation limit is essentially constant may be greater than 50 degrees, greater than 60 degrees, greater than 70 degrees, greater than 80 degrees, or greater than 90 degrees, in some instances.

Figure 8:
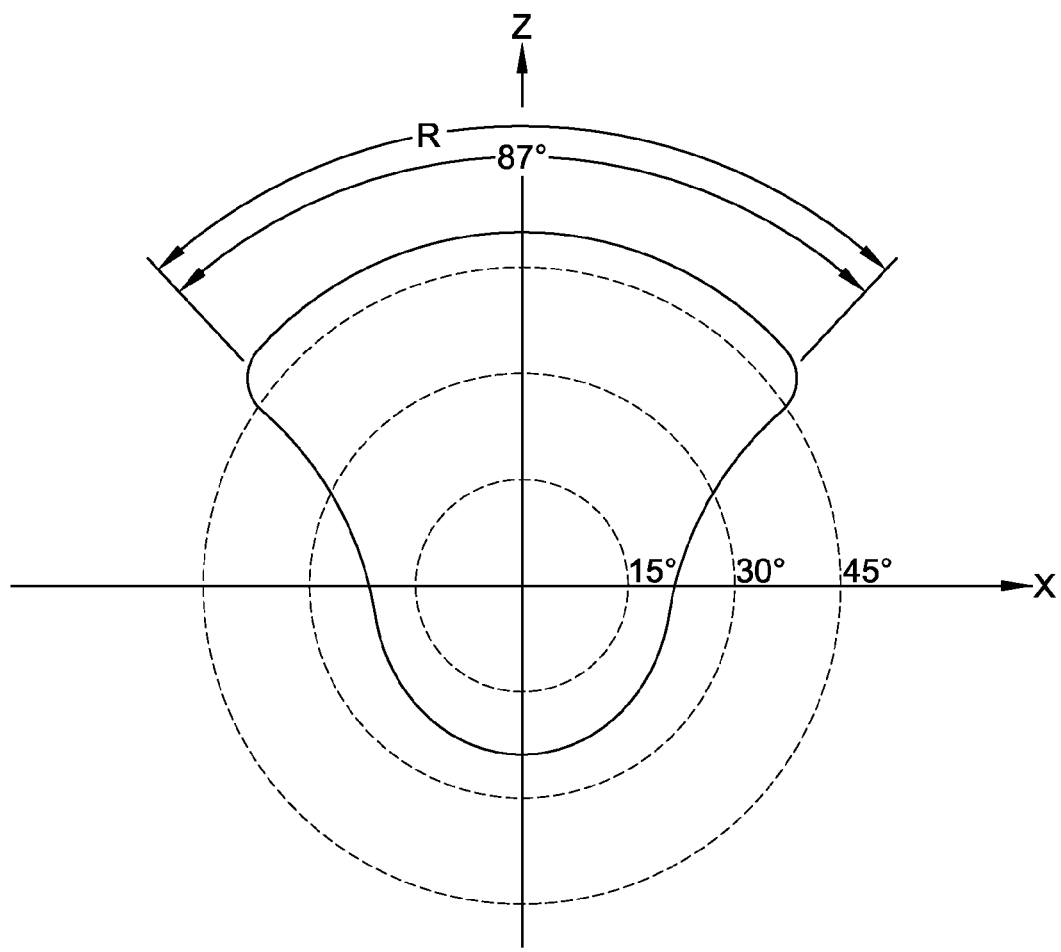
FIG. 8 is an exemplary plot of angulation limit as a function of azimuthal angle (in the x-z plane) around a longitudinal axis of the bore of the housing.
Figure 9:
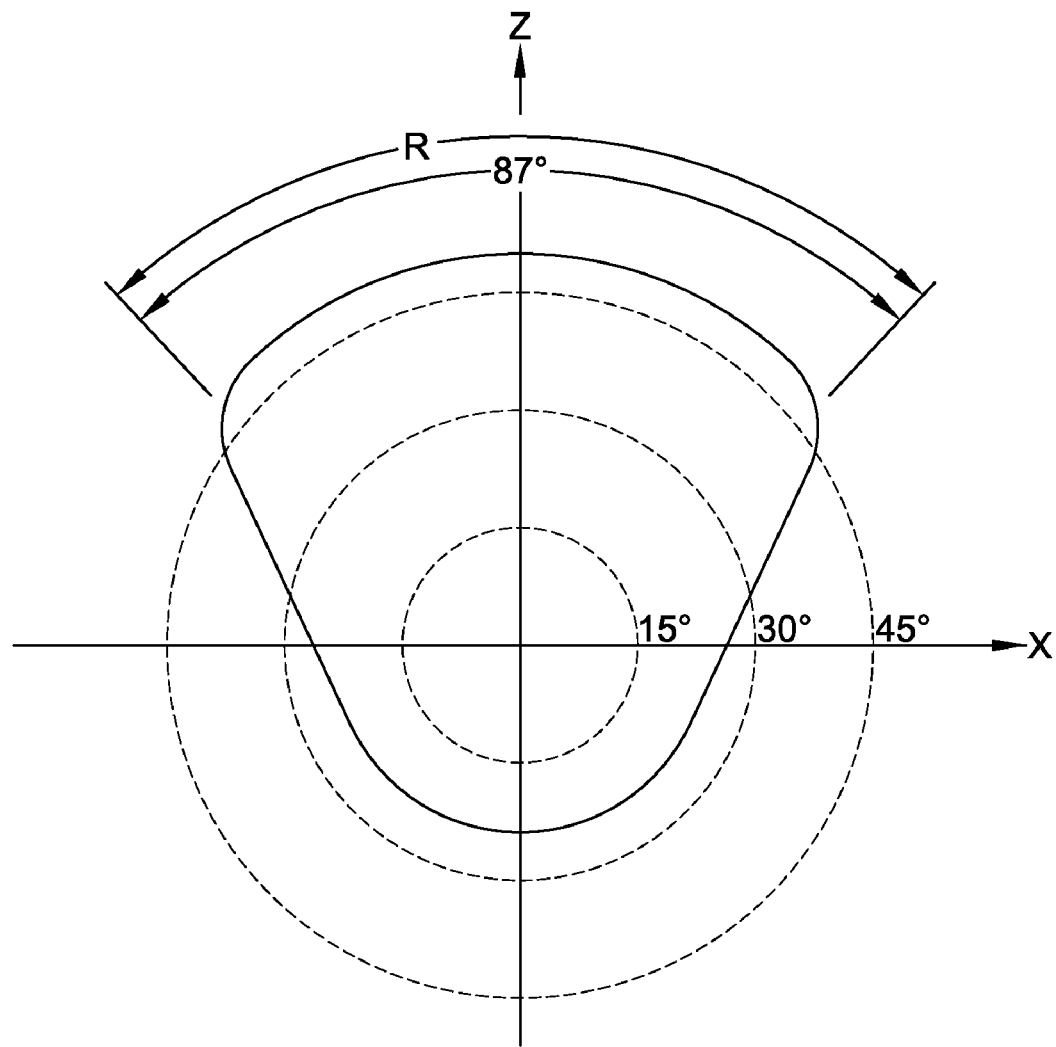
FIG. 9 is another exemplary plot of angulation limit as a function of azimuthal angle (in the x-z plane) around a longitudinal axis of the bore of the housing.

FIGS. 8 and 9 are two exemplary plots of angulation limit as a function of azimuthal angle (in the x-z plane) around a longitudinal axis of the bore of the housing 30. In both of these plots, the longitudinal axis of the housing 30 lies along the y-axis, with azimuthal angles tracing out 360 degrees in the x-z plane. In each of these, the low-angulation direction 53 is along the negative z-axis (or at 6 o'clock or 180 degrees on the plots), and the high-angulation direction 54 is along the positive z-axis (or at 12 o'clock or 0 degrees on the plots). For each azimuthal angle (tracing out a full 360 degrees), the angulation limit at the particular azimuthal angle has a value given by the plotted curve.

FIG. 8, which plots the angulation limits provided by the opening 56 of the housing 30, shows exemplary angulation limit values of 25.3 degrees in the low-angulation direction 53 (6 o'clock or 180 degrees on the plot), 17.3 degrees lateral to the low-angulation direction 53 (3 o'clock or 90 degrees and 9 o'clock or 270 degrees on the plot), and 47.5 degrees in the high-angulation direction 54 (12 o'clock or 0 degrees on the plot). Note that the angulation limit is essentially constant over a range of azimuthal angles R of 87 degrees centered about the high-angulation direction 54, corresponding to the ridge 55 along the perimeter of the aperture on the bottom surface 51 of the housing 30.

FIG. 9 differs from FIG. 8 primarily in the shape of the side walls 52. Compared to the side walls 52 that generated the curve in FIG. 8, the side walls 52 of the opening 56 may curve outwardly (i.e., concave), resulting in a plot of angulation limits corresponding more closely to FIG. 9. As a result, the angulation limit may increase monotonically from the low-angulation direction 53 to the high-angulation direction 54, without reaching a minimum at an intermediate azimuthal angular position. Thus, the minimum angulation limit may be the low-angulation direction 53.

Figure 10:
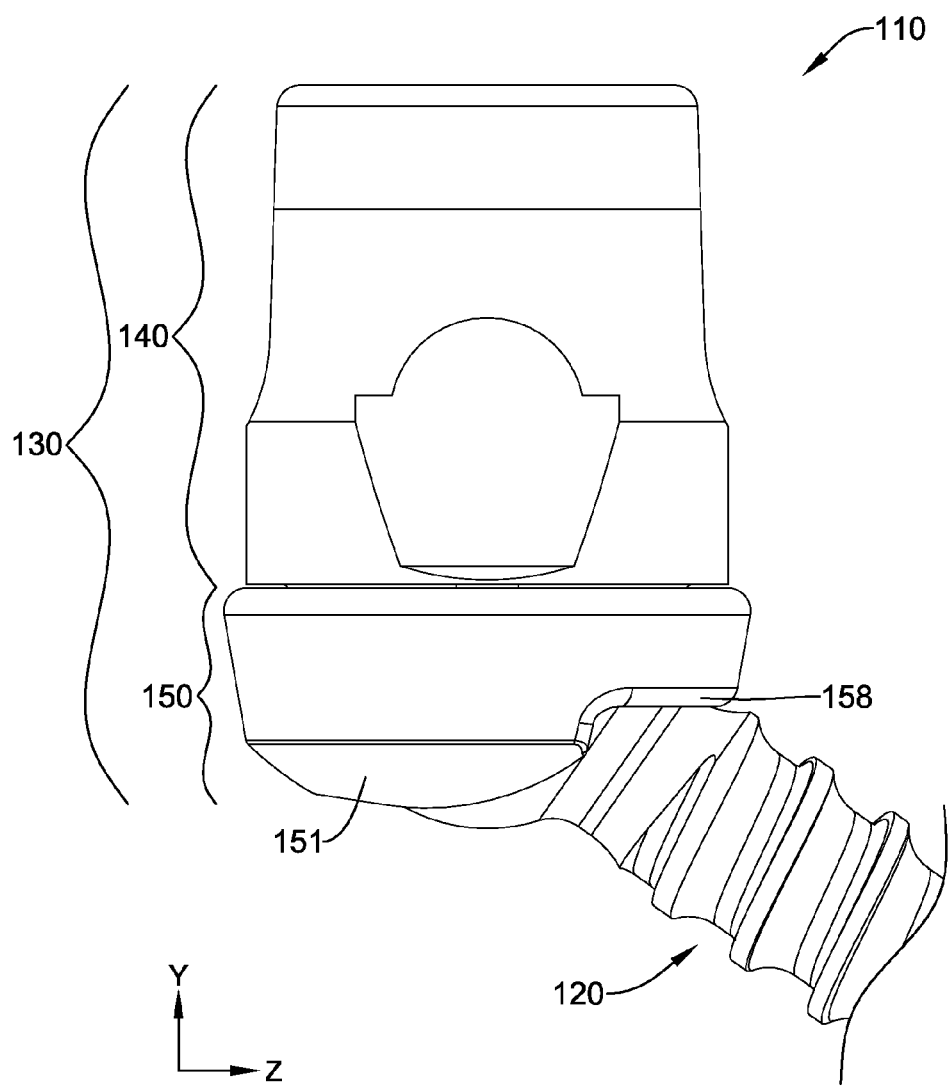
FIG. 10 is a plan view of another exemplary polyaxial bone anchor, viewed from a side.

FIG. 10 is a side view of another exemplary polyaxial bone anchor 110. The anchor 110 has a modular housing 130 formed with an upper housing 140 and lower housing 150. A lower surface 151 of the lower housing 150 has an aperture, through which a shank of the bone screw 120 extends.

In particular, the aperture includes an increased notch 158 that further extends along a lateral side of the housing 130, thereby allowing additional angulation in the high-angulation direction. Such a notch may optionally include a generally flat ridge in the lateral side of the housing 130.

Figure 11:
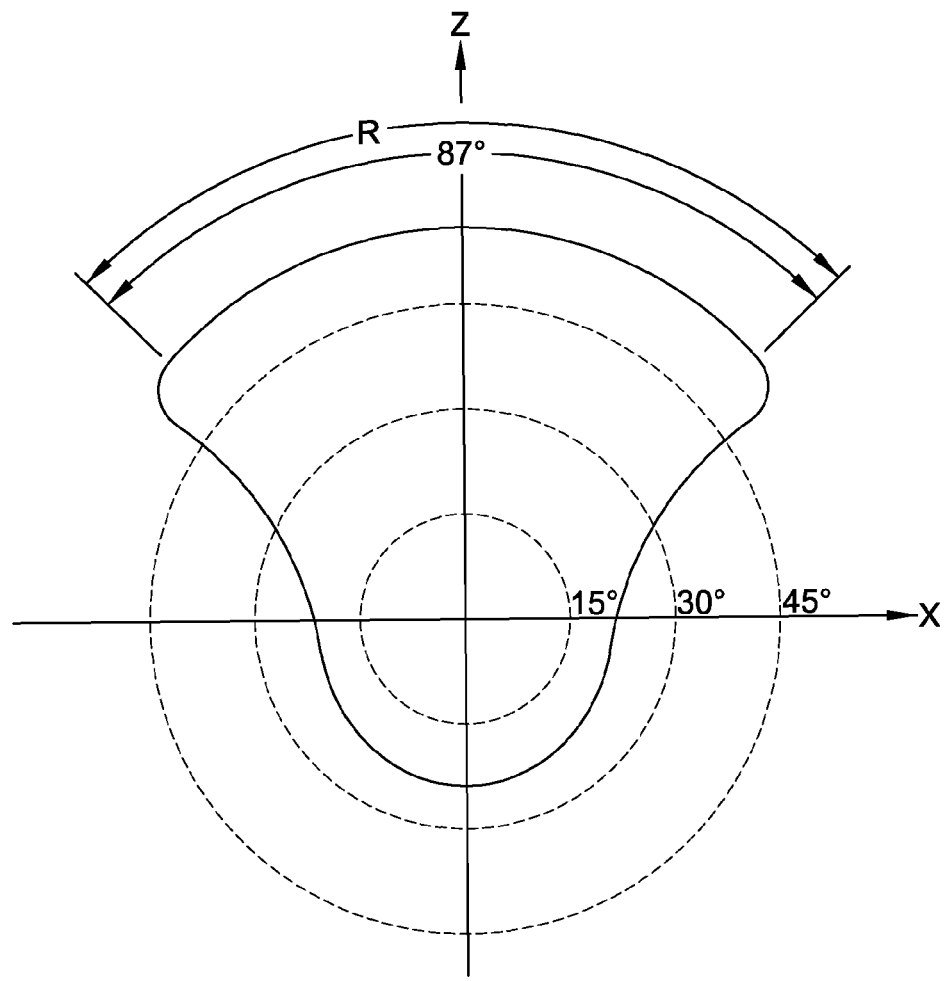
FIG. 11 is an exemplary plot of angulation limit as a function of azimuthal angle (in the x-z plane) around a longitudinal axis of the bore of the housing, for the polyaxial bone anchor of FIG. 10.

FIG. 11 is an exemplary plot of angulation limit as a function of azimuthal angle (in the x-z plane) around a longitudinal axis of the bore of the housing 130, for the housing 130 having the increased notch 158 and shown in FIG. 10. Compared with the plot of FIG. 8, for which the housing 30 lacks an increased notch 158, the plot of FIG. 11 may include a region over which the angulation limit is further increased.

The plot of FIG. 11 shows exemplary angulation limit values of 25.3 degrees in the low-angulation direction (6 o'clock or 180 degrees on the plot), 17.3 degrees lateral to the low-angulation direction (3 o'clock or 90 degrees and 9 o'clock or 270 degrees on the plot), and 55 degrees in the high-angulation direction (12 o'clock or 0 degrees on the plot). Note that the angulation limit is essentially constant over a range of azimuthal angles R of 87 degrees centered about the high-angulation direction, corresponding to the ridge along the perimeter of the aperture at the notch 158 on the bottom surface of the housing 130.

Figure 12:
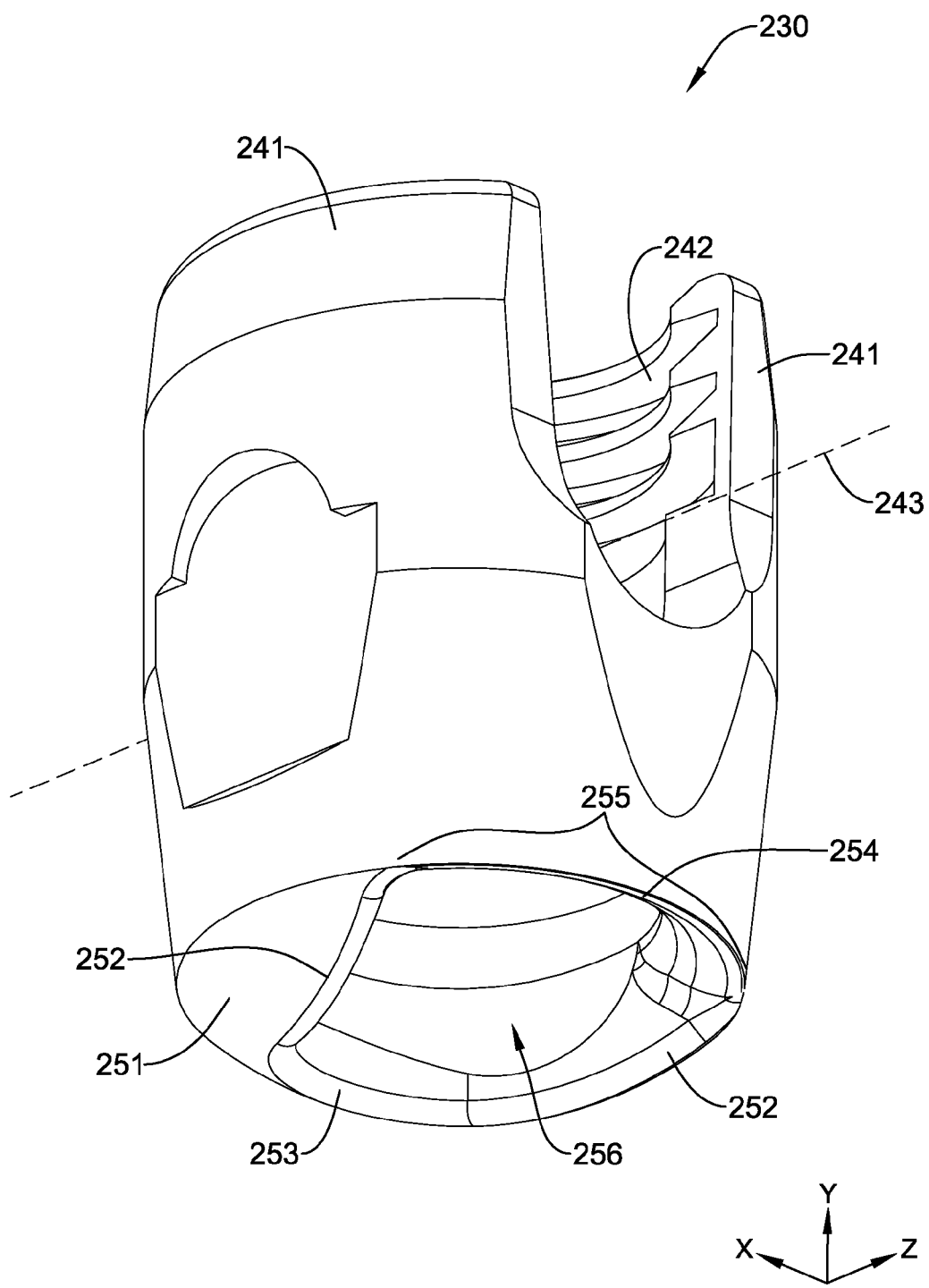
FIG. 12 is a perspective view of an exemplary housing for another polyaxial bone anchor, viewed from below.

FIG. 12 illustrates another exemplary housing 230 for a polyaxial bone anchor. The housing 230 is of a monolithic construction, in contrast with the multi-piece modular housings shown in FIGS. 1-7 and 10.

The housing 230 may include a pair of arms 241 at its upper edge, between which lies a U-shaped channel 243 that may accommodate an elongate member (not shown). There may be threads 242 inside the arms 241 at the upper edge, which may accommodate a fastener or set screw (not shown).

The bottom surface 251 of the housing 230 may also have an opening 256 that defines the angulation limit of the screw (not shown) as a function of azimuthal angle. Such an opening 256 may be similar in shape and function to the opening 56 shown most clearly in FIGS. 3 and 4. For instance, the opening 256 in the bottom surface 251 may be generally V-shaped, with converging side walls 252. At the "closed" end of the V-shape, the angled side walls 252 define a low-angulation direction 253. Opposite the low-angulation direction 253, at the "open" end of the V-shape, the angled side walls 252 define a high-angulation direction 254. There may be a ridge 255 around the high-angulation direction 254, in which the angulation limit may be essentially constant.

Figure 13:
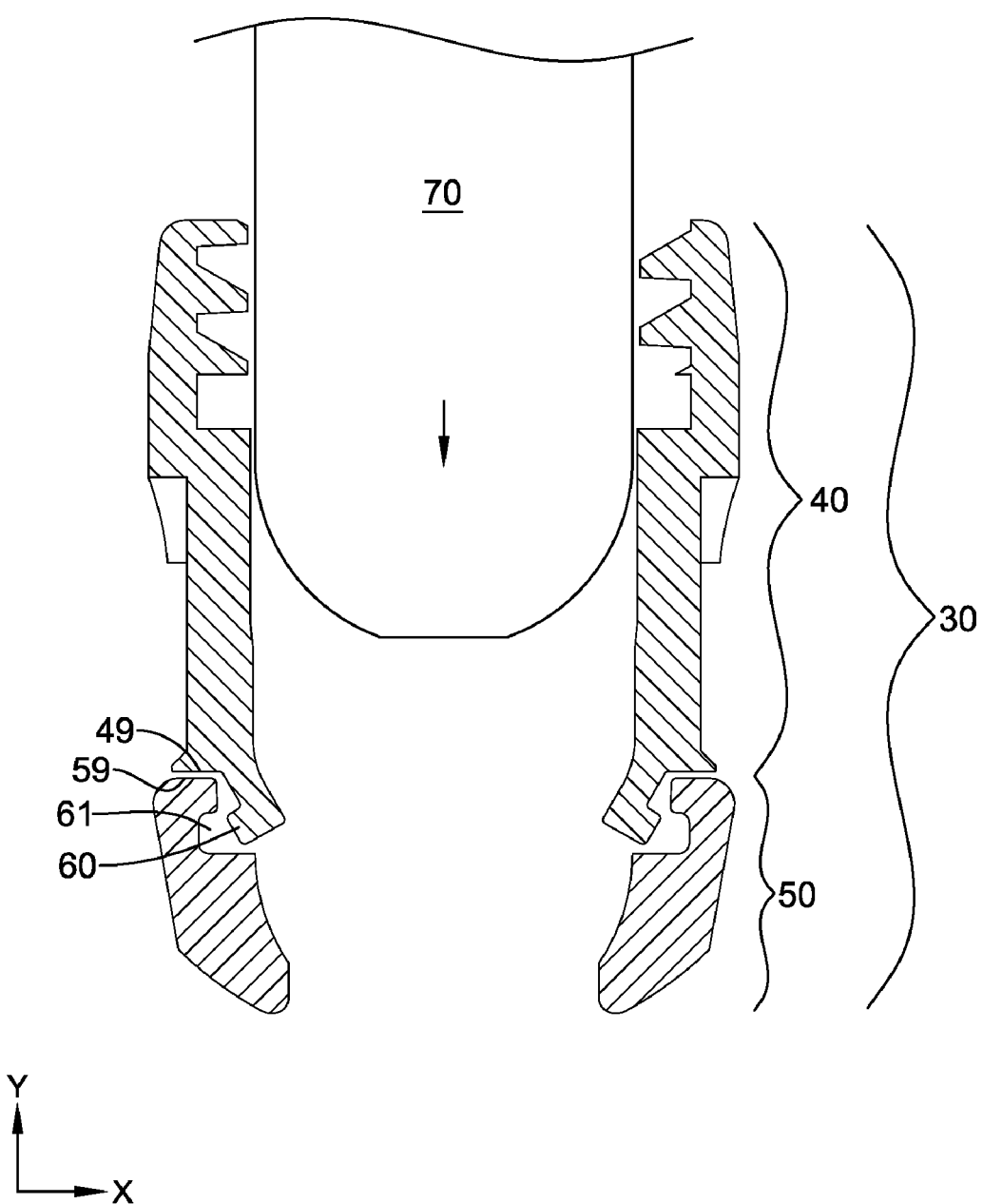
FIGS. 13-14 illustrate an exemplary process of assembling the upper housing with the lower housing.
Figure 14:
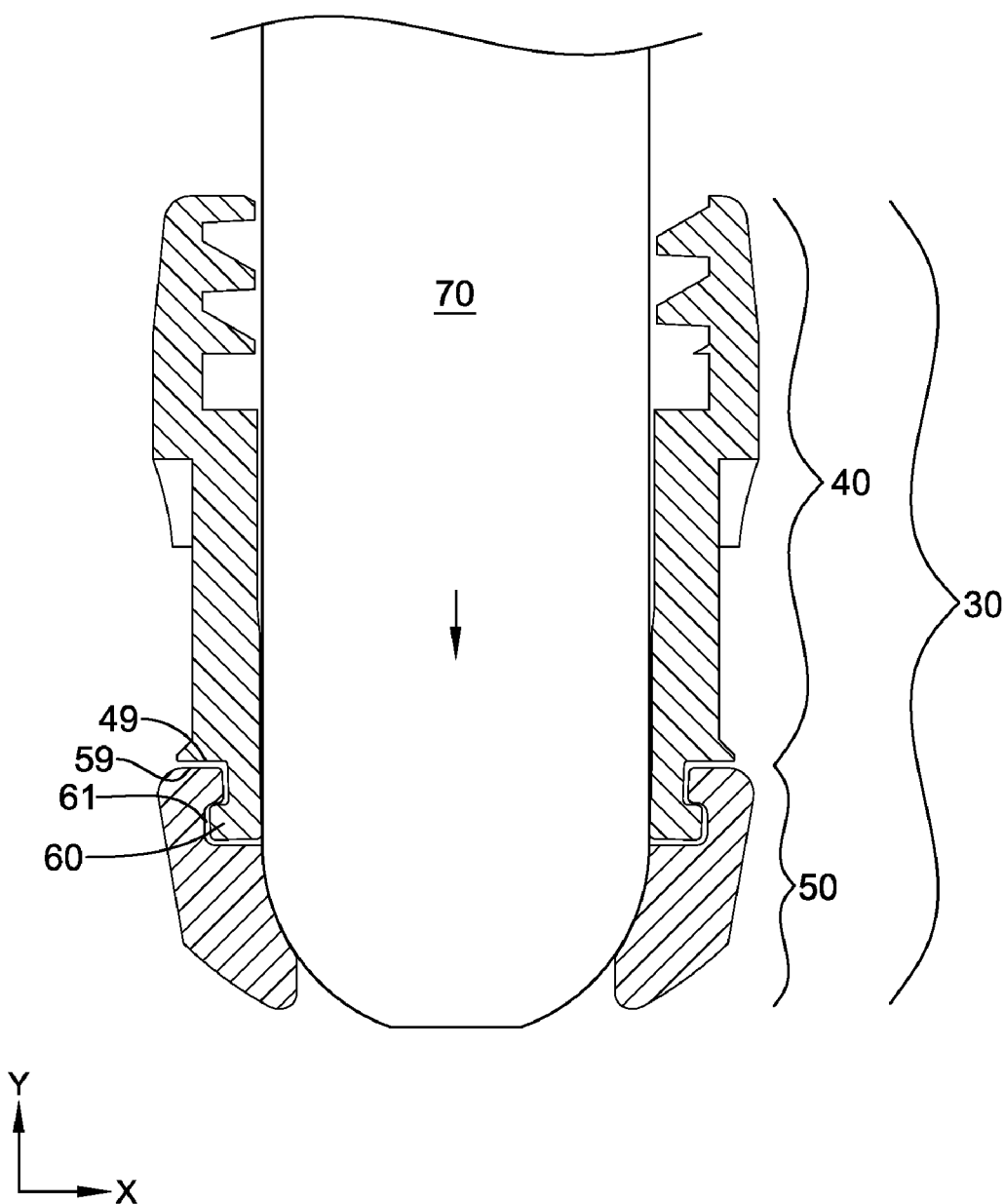
Figure 15:
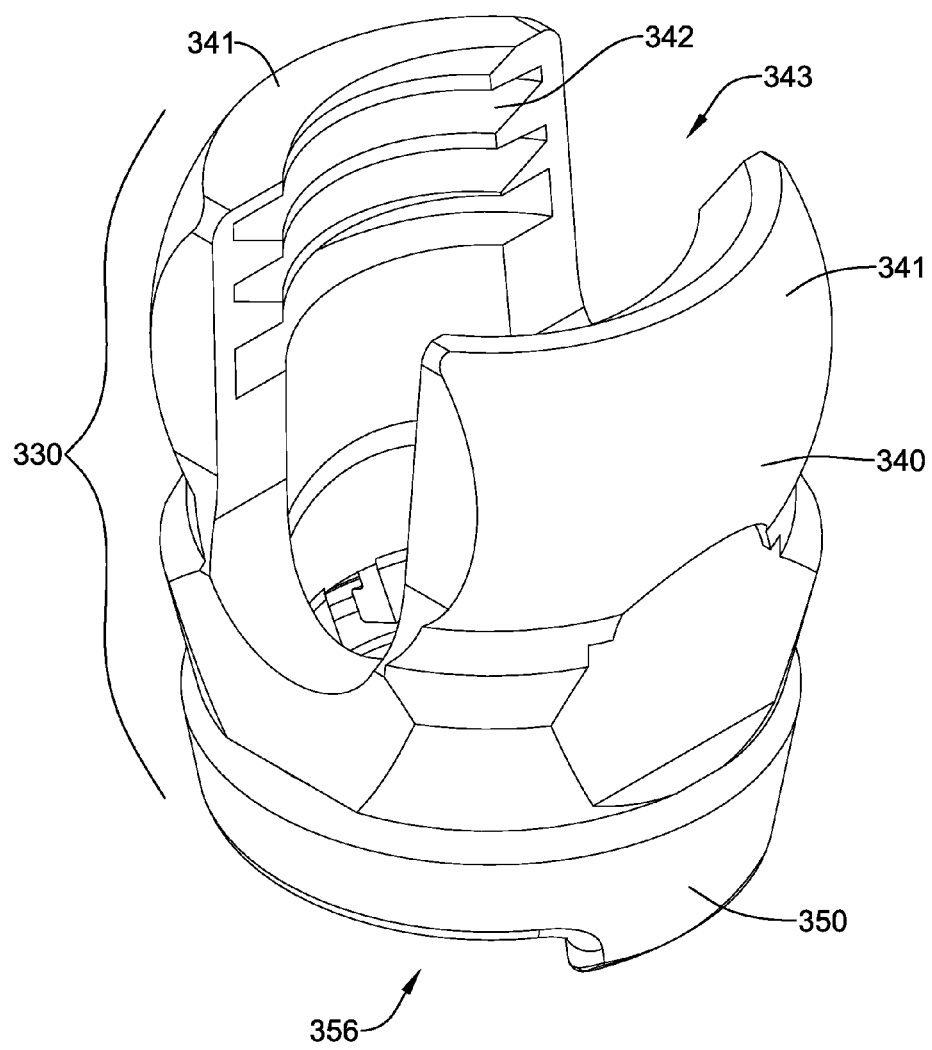
FIGS. 15-18 illustrate an exemplary housing of a polyaxial bone anchor having rotational limits between an upper housing and a lower housing.

Having discussed the way the angulation limit is controlled as a function of azimuthal angle, we turn now to an exemplary way the upper component 40 and lower component 50 of the housing 30 may be assembled, illustrated in FIGS. 13-14.

As illustrated in FIG. 13, the upper housing 40 may include a series of plastically deformable tabs 60 circumferentially arranged around a lower end of the upper housing 40. Each tab 60 may have a portion that extends radially outward beyond a radial extent of the bore of the housing 30, and may also have a portion that extends radially inside the bore. In this particular example, the tabs 60 may be forced radially outward during assembly of the upper housing 40 and the lower housing 50 to couple the upper housing 40 with the lower housing 50.

Radially adjacent to the tabs 60 is a lip 61 at or near the upper end of the lower housing 50. The lip 61 may be circumferentially continuous, or may alternatively be circumferentially discontinuous. In some cases, the lip 61 may be a single edge, the bottom side of which can engage the top side of the tabs 60. In other cases, the lip 61 may be formed as a groove, with both upper and lower edges, so that the tabs 60 may engage between the upper and lower edges of the groove.

During a manufacturing step the tabs 60 on the upper housing 40 may be expanded radially outward to engage the tabs 60 into a lip 61 on the lower housing 50, thereby non-removably joining the upper and lower housings 40, 50 together. The tabs 60 may be manufactured in the radially unexpanded state (e.g., the tabs 60 may initially be oriented in the radially unexpanded state in an equilibrium state), and subsequently plastically deformed via an applied force into the radially expanded state and maintained in the radially expanded state even upon removal of the applied force.

For example, first the upper and lower housings 40, 50 are placed together so that a lower edge 49 of the upper housing 40 is proximate an upper edge 59 of the lower housing 50. Such a placement ensures that the tabs 60 are radially adjacent to the lip 61. The retainer assembly 13 and screw 20 may be absent from the upper housing 40 at this stage.

Next, as shown in FIG. 13, a mandrel 70 is inserted downward into the bore in the upper housing 40. The mandrel 70 may be sized to closely match the bore. The mandrel 70 may contact the portions of the tabs 60 that extend into the interior of the bore. Such portions may be notches, as shown in FIG. 13, or may be other structures, such as inclined surfaces or ramps. As the mandrel 70 moves downward past the tabs 60, as shown in FIG. 14, the tabs 60 may be forced radially outward and plastically deform into a radially outward second configuration. In this particular design, the tabs 60 may bend about their mounted portions, although other suitable plastic deformations may be used to push the tabs 60 into the lip area. Once radially expanded outward by the mandrel 70, the tabs 60 remain in their radially expanded state due to the nature of their plastic deformations even in the absence of the applied force. The mandrel 70 may then be removed. The tabs 60, once radially expanded outwards, may engage the lip 61 on the lower housing 50, and may thereby join the upper housing 40 to the lower housing 50.

In some instances, the tabs 60 and lip 61 may be appropriately sized and configured such that once the tabs 60 are plastically deformed into the lip 61 or groove, the tabs 60 may frictionally contact the head 21 of the bone screw 20 subsequently placed in the housing 30 to provide frictional engagement against the head 21. Such frictional contact may restrict pivotal movement between the housing 30 and the bone screw 20.

In the embodiment shown in FIGS. 1-7, the upper housing 40 may freely rotate a full 360 degrees relative to the lower housing 50. However, in some instances it may be desired that the upper housing 40 be freely rotatable relative to the lower housing 50 throughout angles of rotation less than 360 degrees. For example, the upper housing 40 may freely rotate relative to the lower housing 50 through an angle of rotation of 270° or less, 250° or less, 225° or less, 210° or less, 200° or less, 190° degrees or less, or 180° degrees or less in some instances. In the event the upper housing 40 were rotated beyond this angle of rotation, the lower housing 50 would begin rotating with the upper housing 40. FIGS. 15-25 illustrate three variations of housings which provide limited rotational movement between the upper housing and lower housing through less than 360 degrees.

FIGS. 15-18 illustrate a first housing 330 of a polyaxial bone anchor having rotational limits between an upper housing 340 and a lower housing 350 of less than 360 degrees. It is noted that the bone screw of the polyaxial bone anchor, extending into the housing 330 through the opening 356 and having a head portion rotationally positioned in the housing 330 has been omitted from the figures. However, it is understood that in use the housing 330 would be polyaxially coupled to a bone engaging portion such as a bone screw 20 similar to the polyaxial bone anchor 10 discussed above.

The housing 330 includes a lower housing 350 and an upper housing 340. The upper housing 340 may include a channel 343, such as a U-shaped channel, defined between opposing arms 341 of the upper housing 340 extending from a first side of the upper housing 340 to a second, opposite side of the upper housing 340. The channel 343 may be configured to receive a rod or elongate member inserted into the channel 343 from the top of the housing 330. A threaded fastener may be threadably engaged with the threads 342 formed in the opposing arms 341 to secure the elongate member in the channel 343.

The lower housing 350 may include an opening 356 for receiving a bone screw (not shown) therethrough. Similar to the opening 56, described above, the opening 356 in the lower housing 350 may be generally V-shaped, with angled or converging side walls. Discussion of the opening 56, above, may be applicable to the opening 356. For example, at the "closed" end of the V-shape (i.e., the end in which the side walls are closer together), the angled side walls define a low-angulation direction. Opposite the low-angulation direction, at the "open" end of the V-shape (i.e., the end in which the side walls are further apart), the angled side walls define a high-angulation direction.

The upper housing 340 may be rotatably coupled to the lower housing 350. For example, similar to the housing 30, the upper housing 340 may include a plurality of circumferentially arranged tabs 360 configured to be disposed in an annular groove 361 of the lower housing 350 to couple the upper housing 340 to the lower housing 350.

The housing 330 may also include complementary structure between the upper housing 340 and the lower housing 350 for limiting rotation between the upper housing 340 and the lower housing 350. For example, the upper housing 340 may include a portion which engages a portion of the lower housing 350 once the upper housing 340 has been rotatably oriented to a threshold position relative to the lower housing 350. Thus, further rotation of the upper housing 340 results in corresponding rotation of the lower housing 350.

Figure 16:
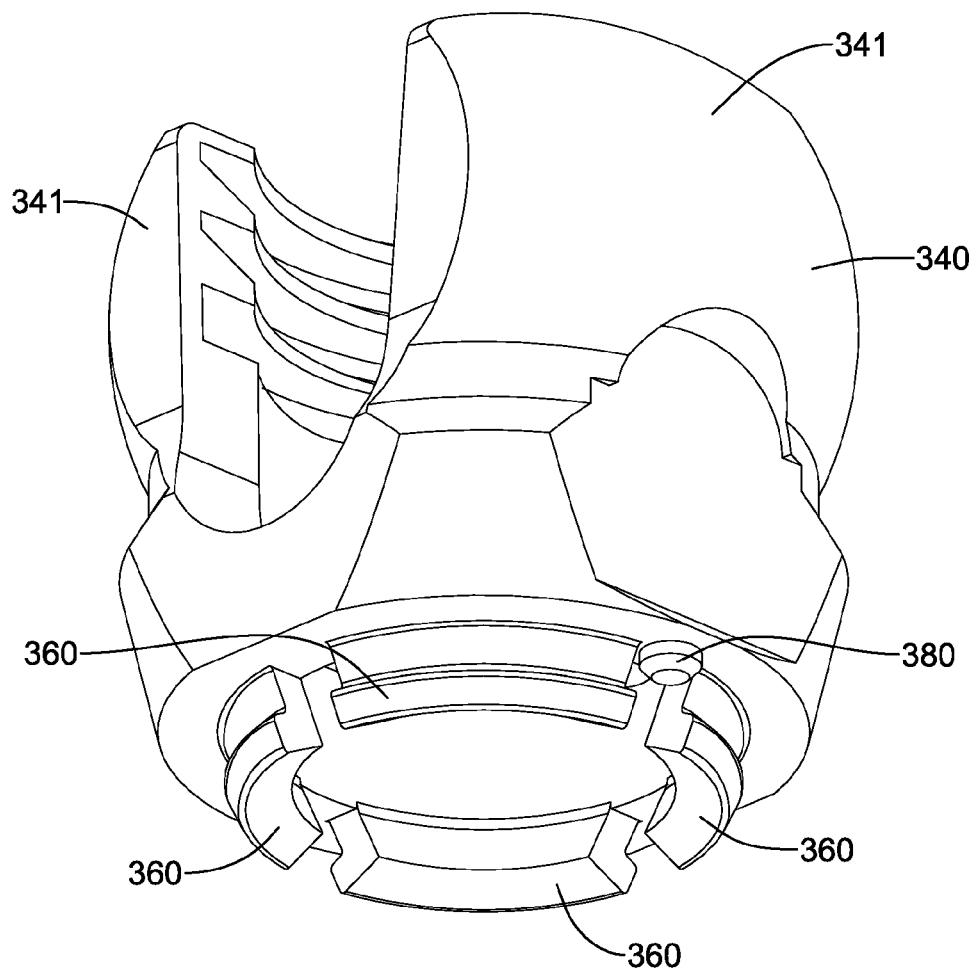
Figure 17:
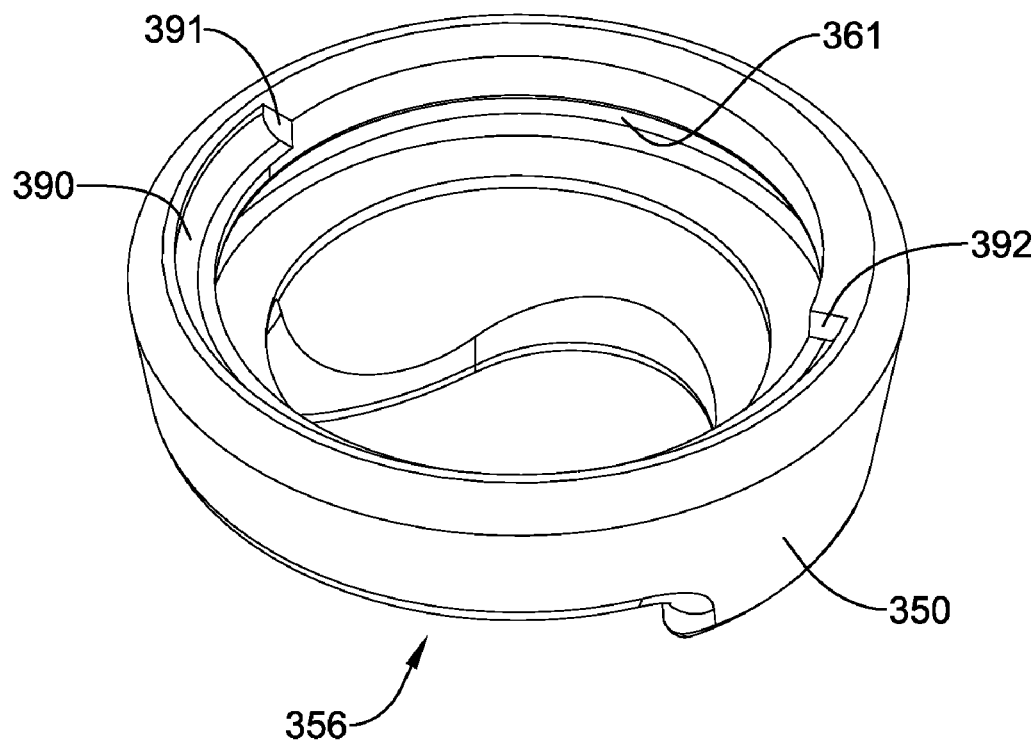
Figure 18:
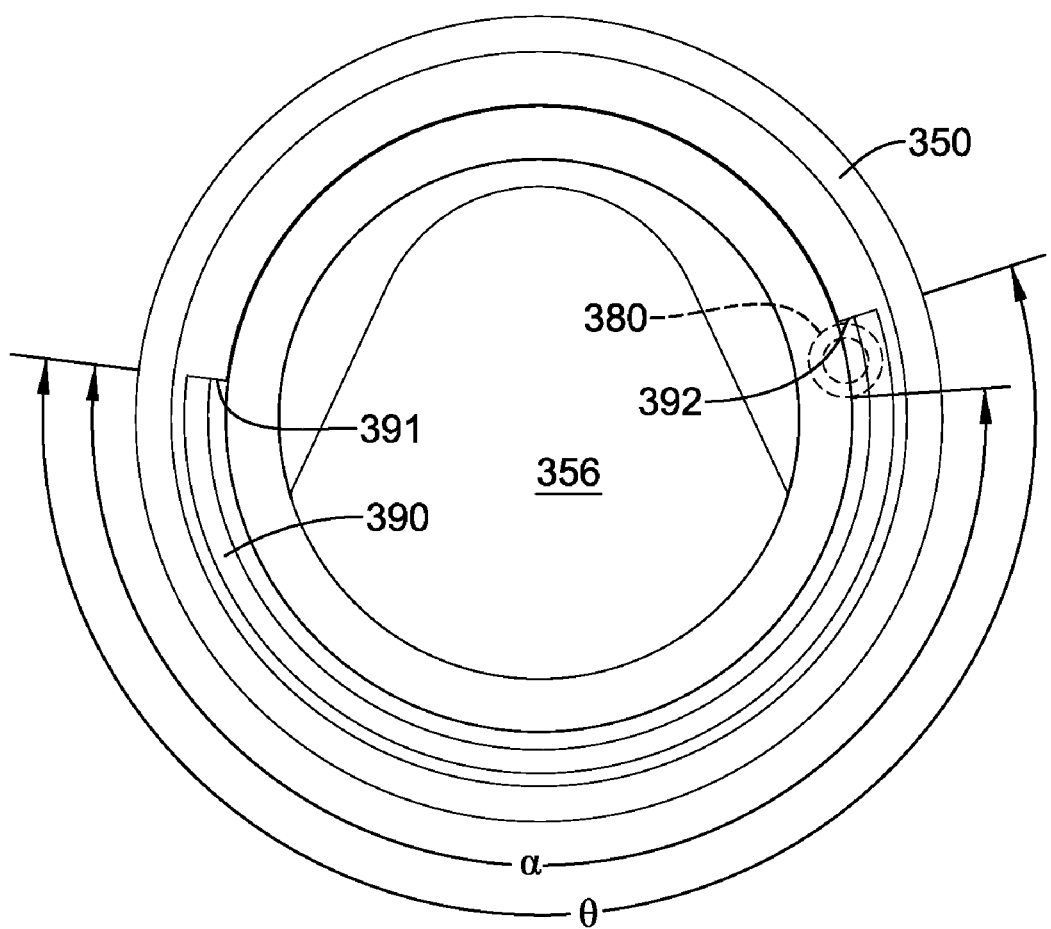

One possible complementary structure is shown in FIGS. 16-18. As shown in FIG. 16, the upper housing 340 may include a protuberance, shown as a pin 380 configured to travel in a groove 390 formed in the lower housing 350, shown in FIG. 17. The pin 380 may extend downwardly from a lower surface of the upper housing 340. The groove 390, shown in FIG. 17, may extend circumferentially around the lower housing 350 less than the full circumference of the lower housing 350. For example, the groove 390, which may be open to the upper surface and/or bore of the lower housing 350, may have a first end surface 391 at a first end of the groove 390 and a second end surface 392 at a second end of the groove 390, thus making the groove 390 continuous for less than the full circumference of the lower housing 350. In some instances, the groove 390 may extend through an angle θ (shown in FIG. 18) of 270° or less, 250° or less, 225° or less, 210° or less, 200° or less, 190° degrees or less, or 180° degrees or less around the circumference of the lower housing 350.

When the lower housing 350 is rotatably coupled to the upper housing 340, the pin 380 is positioned in and travels along the groove 390 between the first end surface 391 and the second end surface 392. As shown in FIG. 18, the pin 380 may travel in the groove 390 through an angle α, which may be less than the angle θ taking into account the width of the pin 380. In some instances, the angle α of travel of the pin 380 in the groove 390 may be 270° or less, 250° or less, 225° or less, 210° or less, 200° or less, 190° degrees or less, or 180° degrees or less. In some instances, it may be desirable to configure the housing 330 such that the angle α of travel of the pin 380 in the groove 390 may be at least 180°, to ensure all possible orientations of the channel 343 relative to the high-angulation direction and/or low-angulation direction of the V-shaped opening 356 in the lower housing 350 may be attained.

The pin 380 may freely travel in the groove 390 between a first position, or first stop point, in which the pin 380 contacts the first end surface 391 to a second position, or second stop point, in which the pin 380 contacts the second end surface 392 without corresponding rotation of the lower housing 350. Further rotation of the upper housing 340 in the same direction once the pin 380 is rotated into contact with either the first end surface 391 or the second end surface 392 results in corresponding rotation of the lower housing 350 with the upper housing 340.

Figure 19:
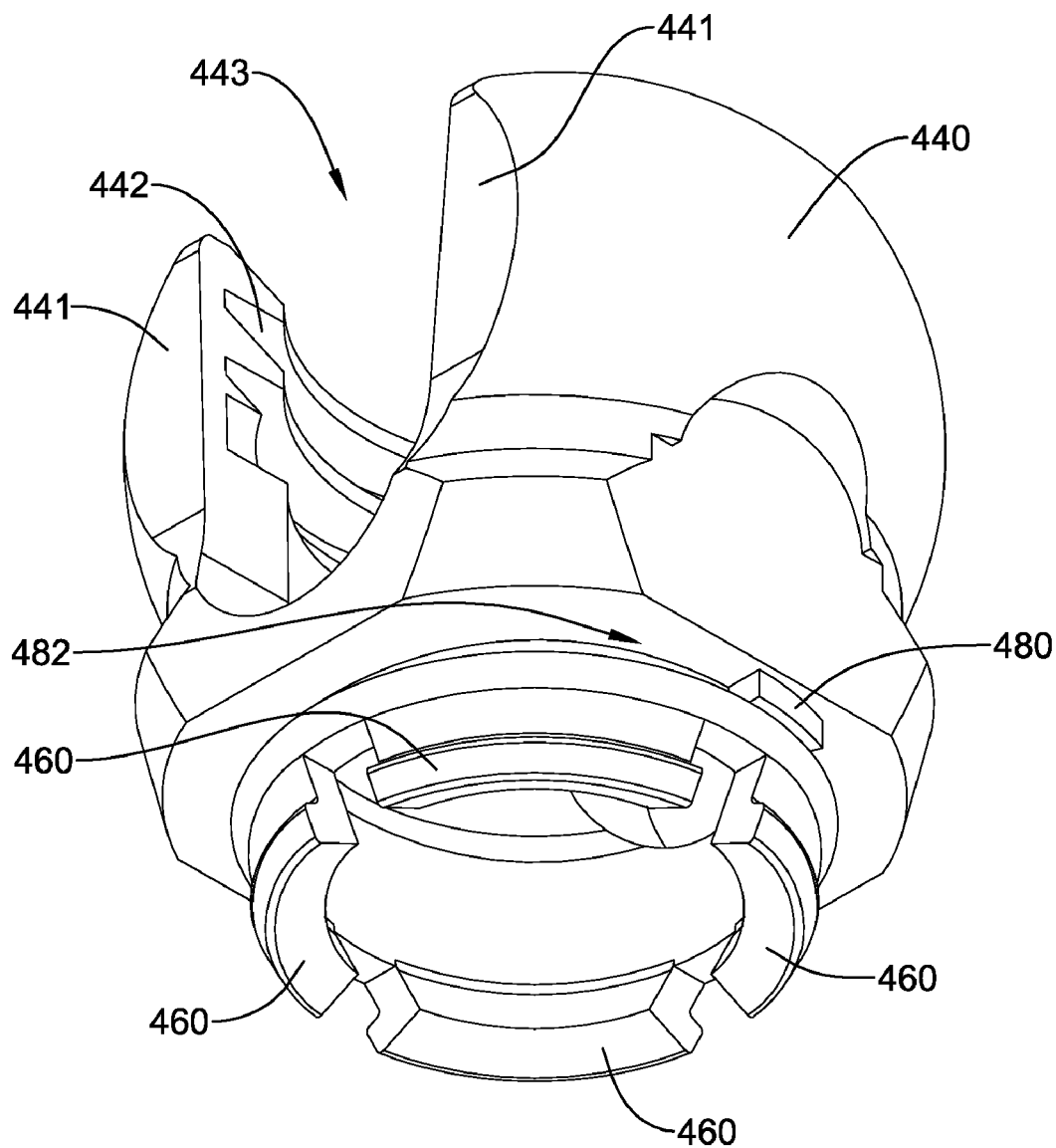
FIGS. 19-21 illustrate another exemplary housing of a polyaxial bone anchor having rotational limits between an upper housing and a lower housing.
Figure 20:
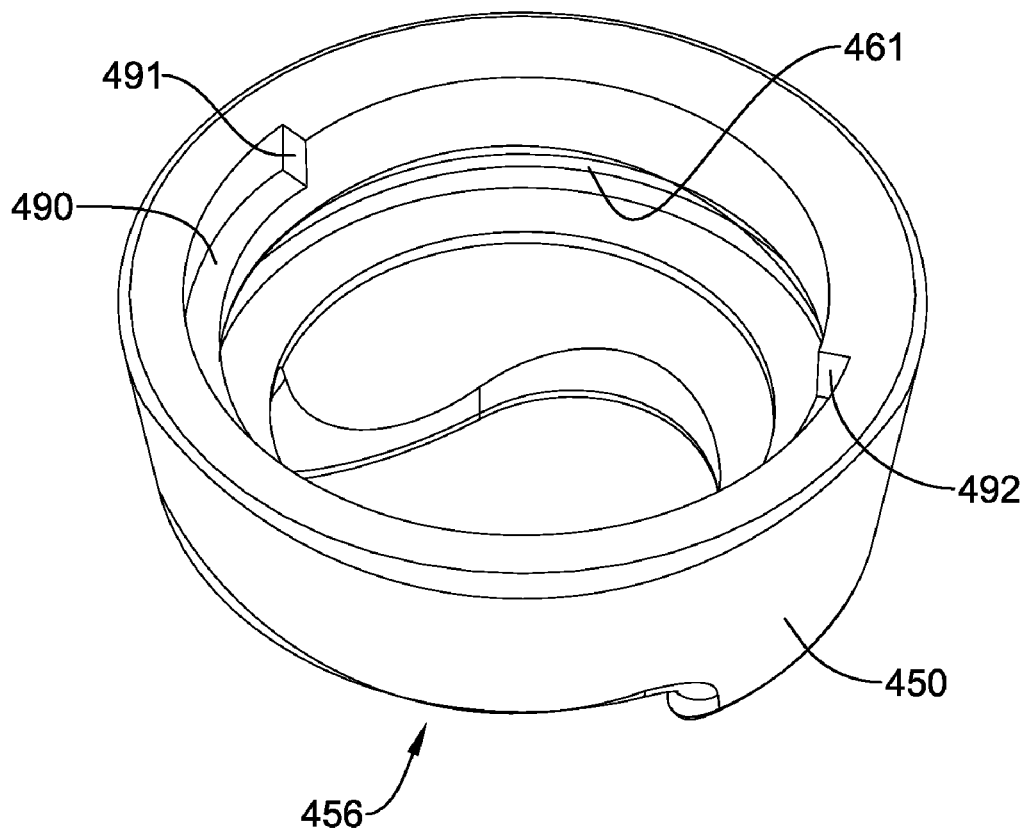
Figure 21:
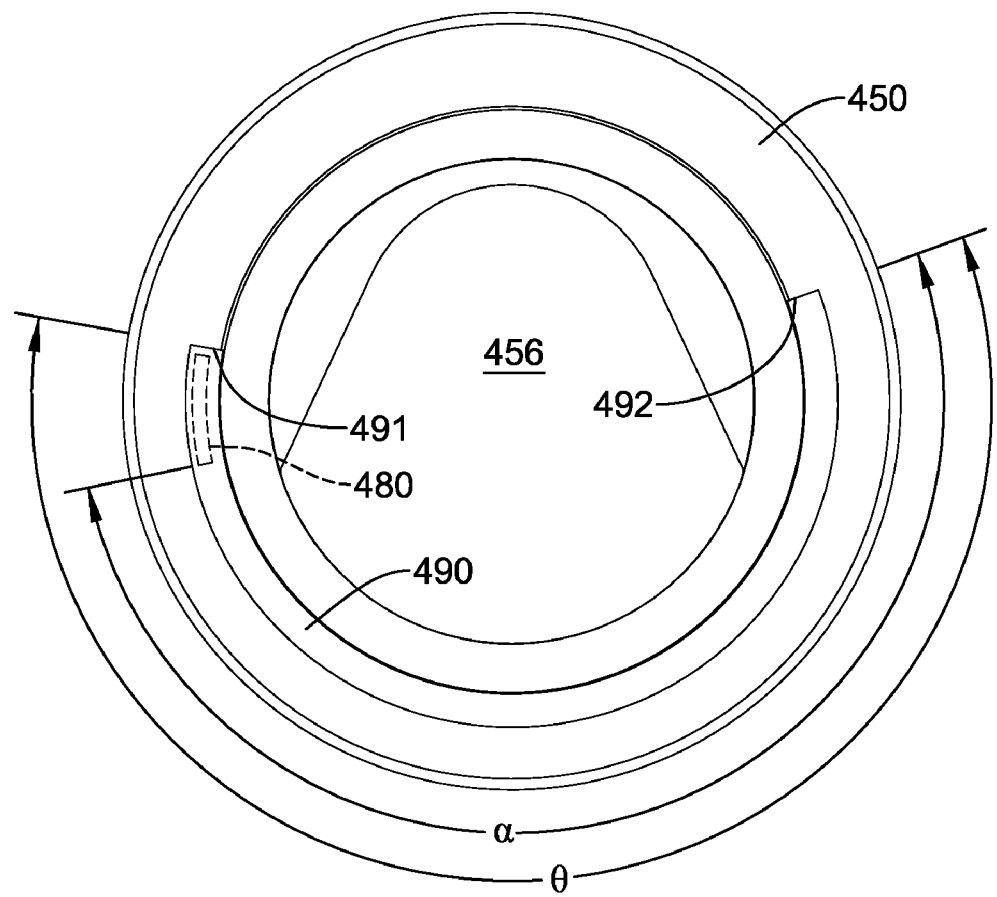
Figure 22:
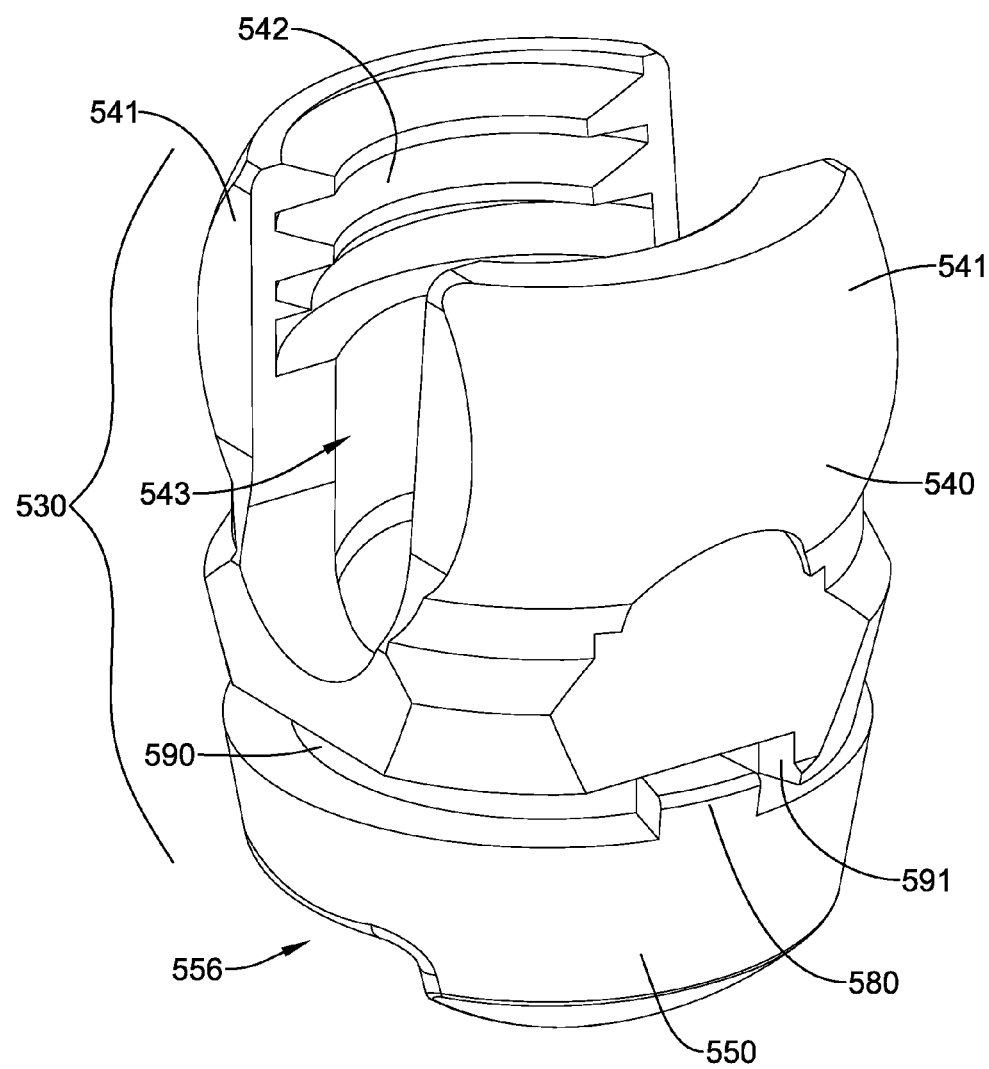
FIGS. 22-25 illustrate yet another exemplary housing of a polyaxial bone anchor having rotational limits between an upper housing and a lower housing.
Figure 23:
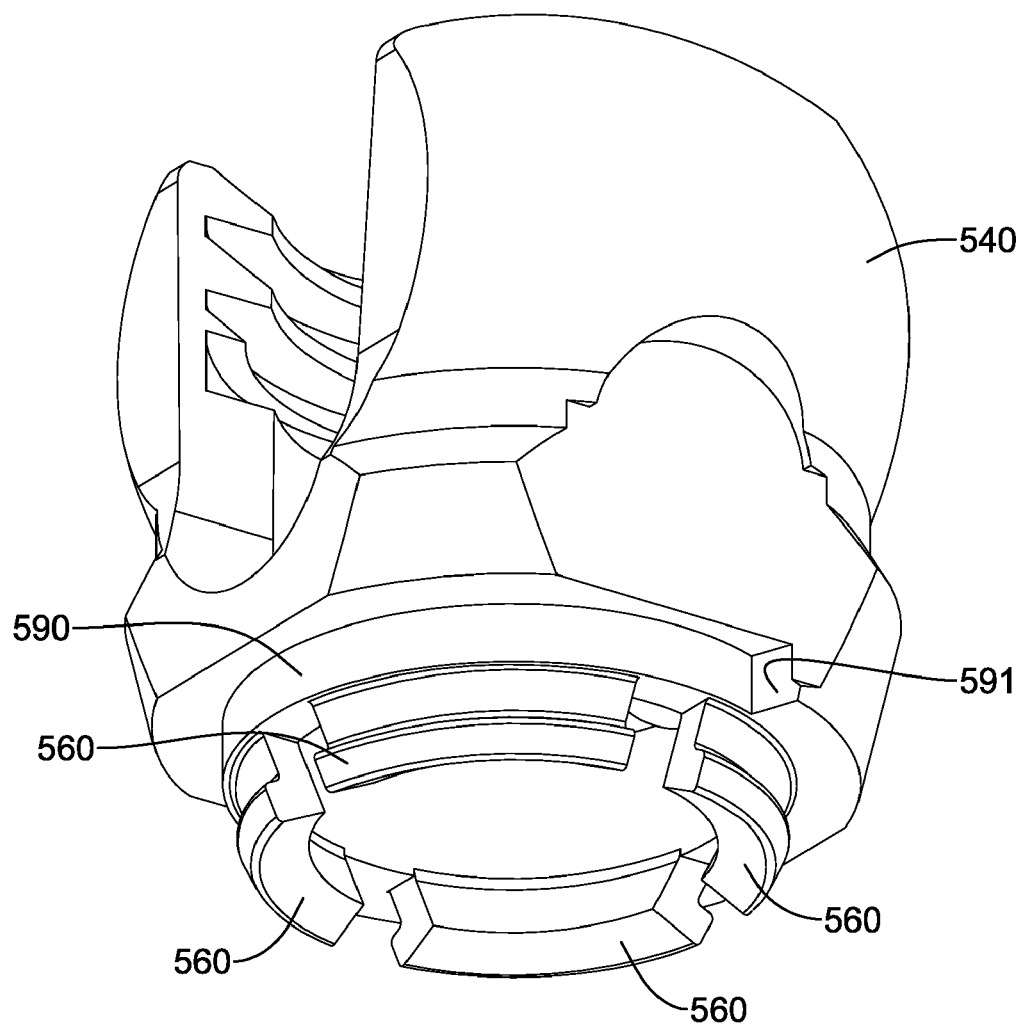

FIGS. 19-21 illustrate the components of another housing of a polyaxial bone anchor having rotational limits between an upper housing 440 (shown in FIG. 19) and a lower housing 450 (shown in FIG. 20) of less than 360 degrees. When assembled together, the housing formed by the upper housing 440 and lower housing 450 may resemble that shown in FIG. 15. It is noted that the bone screw of the polyaxial bone anchor, extending into the housing through the opening 456 of the lower housing 450 and having a head portion rotationally positioned in the housing has been omitted from the figures. However, it is understood that in use the housing formed of the upper housing 440 and lower housing 450 would be polyaxially coupled to a bone engaging portion such as a bone screw 20 similar to the polyaxial bone anchor 10 discussed above.

The upper housing 440 may include a channel 443, such as a U-shaped channel, defined between opposing arms 441 of the upper housing 440 extending from a first side of the upper housing 440 to a second, opposite side of the upper housing 440. The channel 443 may be configured to receive a rod or elongate member inserted into the channel 443 from the top of the housing 430. A threaded fastener may be threadably engaged with the threads 442 formed in the opposing arms 441 to secure the elongate member in the channel 443.

The lower housing 450 may include an opening 456 for receiving a bone screw (not shown) therethrough. Similar to the opening 56, described above, the opening 456 in the lower housing 450 may be generally V-shaped, with angled or converging side walls. Discussion of the opening 56, above, may be applicable to the opening 456. For example, at the "closed" end of the V-shape (i.e., the end in which the side walls are closer together), the angled side walls define a low-angulation direction. Opposite the low-angulation direction, at the "open" end of the V-shape (i.e., the end in which the side walls are further apart), the angled side walls define a high-angulation direction.

The upper housing 440 may be rotatably coupled to the lower housing 450. For example, similar to the housing 30, the upper housing 440 may include a plurality of circumferentially arranged tabs 460 configured to be disposed in an annular groove 461 of the lower housing 450 to couple the upper housing 440 to the lower housing 450.

The upper housing 440 and lower housing 450 may also include complementary structure between the upper housing 440 and the lower housing 450 for limiting rotation between the upper housing 440 and the lower housing 450. For example, the upper housing 440 may include a portion which engages a portion of the lower housing 450 once the upper housing 440 has been rotatably oriented to a threshold position relative to the lower housing 450. Thus, further rotation of the upper housing 440 results in corresponding rotation of the lower housing 450.

One possible complementary structure is shown in FIGS. 19-21. As shown in FIG. 19, the upper housing 440 may include a protuberance, shown as a block 380 configured to travel in a groove 490 formed in the lower housing 450, shown in FIG. 20. The block 480 may extend outwardly from a surface of the upper housing 440. For instance, the block 480 may extend radially outward from a recessed portion 482 of the upper housing 440. The groove 490, shown in FIG. 20, may extend circumferentially around the lower housing 450 less than the full circumference of the lower housing 450. For example, the groove 490, which may be open to the upper surface and/or bore of the lower housing 450, may have a first end surface 491 at a first end of the groove 490 and a second end surface 492 at a second end of the groove 490, thus making the groove 490 continuous for less than the full circumference of the lower housing 450. In some instances, the groove 490 may extend through an angle θ (shown in FIG. 21) of 270° or less, 250° or less, 225° or less, 210° or less, 200° or less, 190° degrees or less, or 180° degrees or less around the circumference of the lower housing 450.

When the lower housing 450 is rotatably coupled to the upper housing 440, the block 480 is positioned in and travels along the groove 490 between the first end surface 491 and the second end surface 492. As shown in FIG. 21, the pin 480 may travel in the groove 490 through an angle α, which may be less than the angle θ taking into account the width of the block 480. In some instances, the angle α of travel of the block 480 in the groove 490 may be 270° or less, 250° or less, 225° or less, 210° or less, 200° or less, 190° degrees or less, or 180° degrees or less. In some instances, it may be desirable to configure the upper housing 440 and lower housing 450 such that the angle α of travel of the block 480 in the groove 490 may be at least 180°, to ensure all possible orientations of the channel 443 relative to the high-angulation direction and/or low-angulation direction of the V-shaped opening 456 in the lower housing 450 may be attained.

The block 480 may freely travel in the groove 490 between a first position, or first stop point, in which the block 480 contacts the first end surface 491 to a second position, or second stop point, in which the block 480 contacts the second end surface 492 without corresponding rotation of the lower housing 450. Further rotation of the upper housing 440 in the same direction once the block 480 is rotated into contact with either the first end surface 491 or the second end surface 492 results in corresponding rotation of the lower housing 450 with the upper housing 440.

FIGS. 22-25 illustrate a third housing 530 of a polyaxial bone anchor having rotational limits between an upper housing 540 and a lower housing 550 of less than 360 degrees. It is noted that the bone screw of the polyaxial bone anchor, extending into the housing 530 through the opening 556 and having a head portion rotationally positioned in the housing 530 has been omitted from the figures. However, it is understood that in use the housing 530 would be polyaxially coupled to a bone engaging portion such as a bone screw 20 similar to the polyaxial bone anchor 10 discussed above.

The housing 530 includes a lower housing 550 and an upper housing 540. The upper housing 540 may include a channel 543, such as a U-shaped channel, defined between opposing arms 541 of the upper housing 540 extending from a first side of the upper housing 540 to a second, opposite side of the upper housing 540. The channel 543 may be configured to receive a rod or elongate member inserted into the channel 543 from the top of the housing 530. A threaded fastener may be threadably engaged with the threads 542 formed in the opposing arms 541 to secure the elongate member in the channel 543.

The lower housing 550 may include an opening 556 for receiving a bone screw (not shown) therethrough. Similar to the opening 56, described above, the opening 556 in the lower housing 550 may be generally V-shaped, with angled or converging side walls. Discussion of the opening 56, above, may be applicable to the opening 556. For example, at the "closed" end of the V-shape (i.e., the end in which the side walls are closer together), the angled side walls define a low-angulation direction. Opposite the low-angulation direction, at the "open" end of the V-shape (i.e., the end in which the side walls are further apart), the angled side walls define a high-angulation direction.

The upper housing 540 may be rotatably coupled to the lower housing 550. For example, similar to the housing 30, the upper housing 540 may include a plurality of circumferentially arranged tabs 560 configured to be disposed in an annular groove 561 of the lower housing 550 to couple the upper housing 540 to the lower housing 550.

The housing 530 may also include complementary structure between the upper housing 540 and the lower housing 550 for limiting rotation between the upper housing 540 and the lower housing 550. For example, the upper housing 540 may include a portion which engages a portion of the lower housing 550 once the upper housing 540 has been rotatably oriented to a threshold position relative to the lower housing 550. Thus, further rotation of the upper housing 540 results in corresponding rotation of the lower housing 550.

Figure 24:
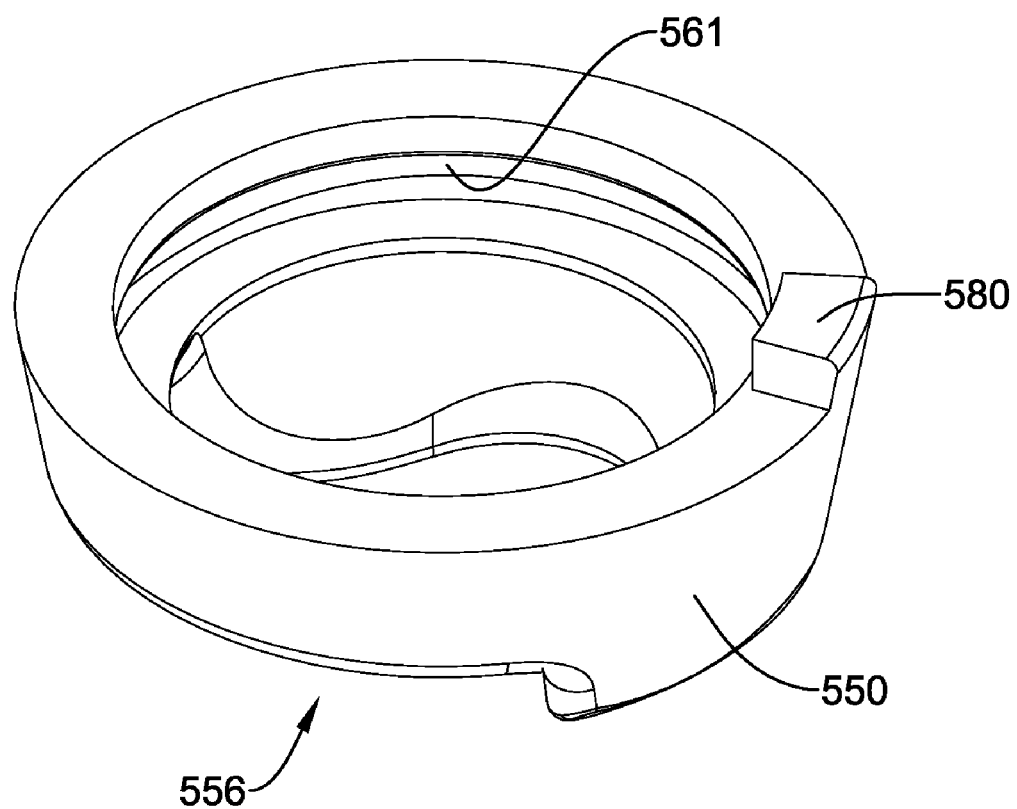

One possible complementary structure is shown in FIGS. 22-25. As shown in FIG. 24, the lower housing 550 may include a protuberance, shown as a projection 580 configured to travel in a groove 590 formed in the upper housing 540, shown in FIG. 23. The projection 580 may extend upwardly from an upper surface of the lower housing 550. The groove 590, shown in FIG. 23, may extend circumferentially around the upper housing 540 less than the full circumference of the upper housing 540. For example, the groove 590, which may be open to the lower surface and/or outer surface of the upper housing 540, may have a first end surface 591 at a first end of the groove 590 and a second end surface 592 (shown in FIG. 25) at a second end of the groove 590, thus making the groove 590 continuous for less than the full circumference of the upper housing 540. In some instances, the groove 590 may extend through an angle θ (shown in FIG. 18) of 270° or less, 250° or less, 225° or less, 210° or less, 200° or less, 190° degrees or less, or 180° degrees or less around the circumference of the upper housing 540.

Figure 25:
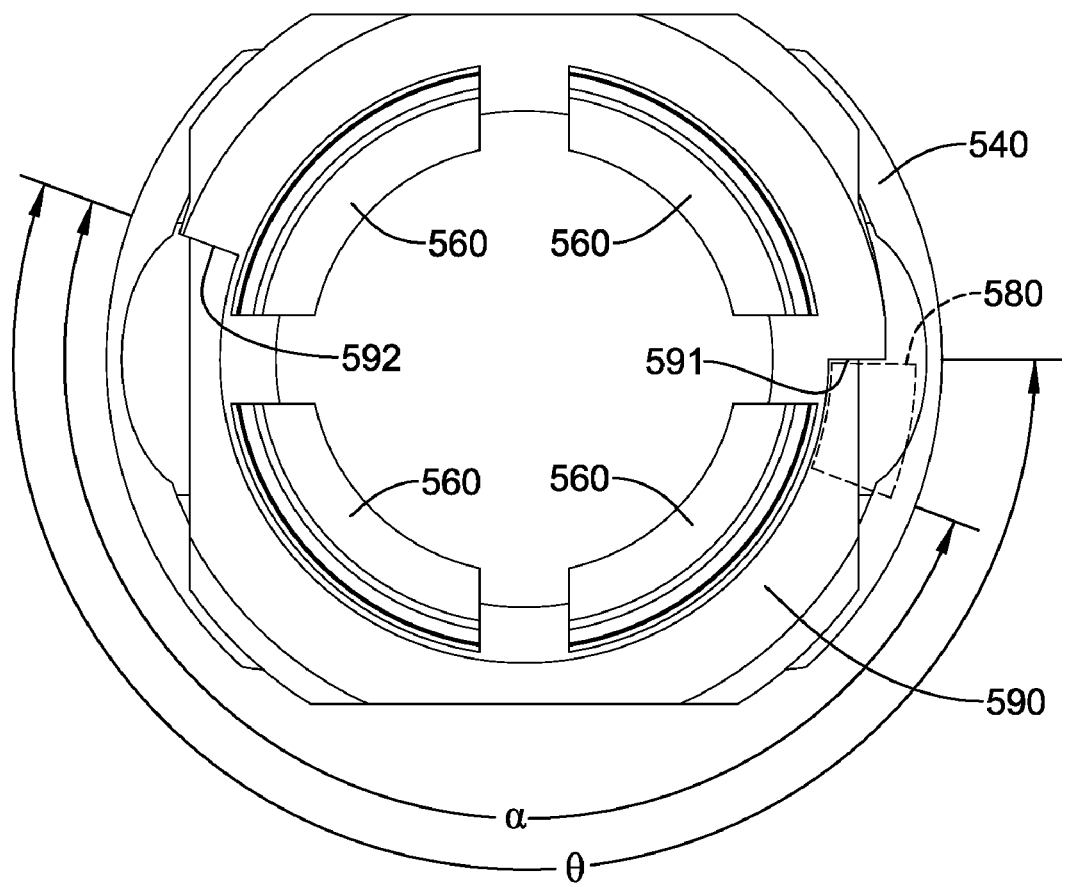

When the lower housing 550 is rotatably coupled to the upper housing 540, the projection 580 is positioned in and travels along the groove 590 between the first end surface 591 and the second end surface 592. As shown in FIG. 25, the projection 580 may travel in the groove 590 through an angle α, which may be less than the angle θ taking into account the width of the projection 580. In some instances, the angle α of travel of the projection 580 in the groove 590 may be 270° or less, 250° or less, 225° or less, 210° or less, 200° or less, 190° degrees or less, or 180° degrees or less. In some instances, it may be desirable to configure the housing 530 such that the angle α of travel of the projection 580 in the groove 590 may be at least 180°, to ensure all possible orientations of the channel 543 relative to the high-angulation direction and/or low-angulation direction of the V-shaped opening 556 in the lower housing 550 may be attained.

The projection 580 may freely travel in the groove 590 between a first position, or first stop point, in which the projection 580 contacts the first end surface 591 to a second position, or second stop point, in which the projection 580 contacts the second end surface 592 without corresponding rotation of the lower housing 550. Further rotation of the upper housing 540 in the same direction once the projection 580 is rotated into contact with either the first end surface 591 or the second end surface 592 results in corresponding rotation of the lower housing 550 with the upper housing 540.

Exemplary usage of housings which provide limited rotational movement between the upper housing and lower housing through less than 360 degrees, including those described above and illustrated in FIGS. 15-25, will now be described. While such usage will be described with regard to the housing 330, the discussion may be equally applicable to the usage of the other described embodiments.

With the housing 330 pivotably attached to the bone screw, the medical personnel may secure the bone screw into a bony structure of a patient by rotating the bone screw with a driver, and thus screwing the bone screw into the bony structure. The bone screw may be secured to the bony structure without needing to maintain the housing 330 in any particular rotational orientation.

Once the bone screw has been screwed into the bony structure, the medical personnel may then orient the housing 330 as desired. For instance, the medical personnel may engage the upper housing 340 with a medical instrument configured to be manipulated in order to rotate the upper housing 340. The upper housing 340 may be rotated until the protuberance (e.g., the pin 380) contacts a stop (e.g., one of the first and second end surfaces 391, 392) of the lower housing 350. Thus, further rotation of the upper housing 340 correspondingly rotates the lower housing 350. The upper housing 340 (and thus the lower housing 350) may be further rotated until the high-angulation direction and/or low-angulation direction of the V-shaped opening 356 in the lower housing 350 is positioned in a desired rotational orientation. For instance, the upper housing 340 (and thus the lower housing 350) may be rotated in a first direction until the high-angulation direction of the V-shaped opening 356 (i.e., the base of the V) is positioned in an orientation in which that the greatest angulation between the housing 330 and the bone screw is desired.

Once the lower housing 350 has been rotated to a position in which the V-shaped opening 356 is at a desired orientation to achieve the angulation desired, the upper housing 340 may be rotated in an opposite, second direction in order to orient the longitudinal axis of the channel 343 in a desired orientation without further rotating the lower housing 350, if the channel 343 is not already oriented as desired. Thus, the upper housing 340 may be freely rotated relative to the lower housing 350 in the second direction any desired amount up to the point the protuberance (e.g., the pin 380) contacts the other stop (e.g., the other of the first and second end surfaces 391, 392) of the lower housing 350. In instances in which the housing 330 is configured such that the upper housing 340 may be freely rotated relative to the lower housing 350 through at least 180°, all possible orientations of the channel 343 relative to the high-angulation direction of the V-shaped opening 356 in the lower housing 350 may be attained. Once properly positioned, the elongate member may be inserted into the channel 343 and secured therein with a fastener, such as threaded cap screw, which may simultaneously lock the angle of the housing 330 relative to the bone screw.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of assembling a polyaxial bone anchor, the method comprising:
providing an upper housing having a bore extending vertically therethrough, the upper housing including a plurality of plastically deformable tabs circumferentially around a lower end of the upper housing in a first radially unexpanded state, each tab having a portion that extends radially outward beyond a radial extent of the bore and a portion that extends radially inside the bore in the first radially unexpanded state;
providing a lower housing having a lip proximate an upper end of the lower housing;
placing the lower housing beneath the upper housing so that the lip is radially adjacent the tabs;
inserting a mandrel downward through the bore in the upper housing;

forcing the tabs radially outward with the mandrel to a second radially expanded state, each tab on the upper housing plastically deforming radially outward and engaging the lip on the lower housing; and withdrawing the mandrel from the upper housing, wherein the tabs remain in the second radially expanded state upon withdrawing the mandrel from the upper housing.

2. The method of claim 1, wherein the upper housing is rotatable relative to the lower housing through an angle of rotation of less than 360 degrees.

3. The method of claim 2, further comprising:
positioning a protuberance of one of the upper housing and the lower housing into a groove of the other of the upper housing and the lower housing.

4. The method of claim 3, wherein the groove has a first end surface and a second end surface and the protuberance travels in the groove between the first end surface and the second end surface, wherein rotation between the upper housing and the lower housing is limited by the protuberance contacting either the first end surface of the groove or the second end surface of the groove.

5. The method of claim 4, further comprising:
permitting the protuberance to travel in the groove through at least 180 degrees, but less than 360 degrees.

6. The method of claim 1, further comprising:
inserting a bone screw through a lower opening of the lower housing.

7. The method of claim 6, wherein the lower opening of the lower housing is generally V-shaped, the V-shape having angled side walls that define a low-angulation direction of the bone screw proximate their intersection and define a high-angulation direction of the bone screw opposite the low-angulation direction.

8. The method of claim 7, wherein the lower opening of the lower housing defines an angulation limit of the bone screw for each azimuthal angle around a longitudinal axis of the bore of the upper housing; and
wherein the angulation limit of the bone screw is generally constant over a range of azimuthal angles centered around the high-angulation direction.

9. The method of claim 1, wherein the lip is circumferentially continuous.

10. The method of claim 1, wherein a lower end of the lower housing comprises a generally spherical surface; and
wherein a lower opening of the lower housing comprises an aperture in the generally spherical surface.

* * * * *